US 9,936,860 B2

(12) United States Patent
Okamoto et al.

(10) Patent No.: US 9,936,860 B2
(45) Date of Patent: Apr. 10, 2018

(54) BENDING APPARATUS

(71) Applicant: OLYMPUS CORPORATION, Tokyo (JP)

(72) Inventors: Yasuhiro Okamoto, Hino (JP); Hiroki Moriyama, Akishima (JP)

(73) Assignee: OLYMPUS CORPORATION, Tokyo (JP)

( * ) Notice: Subject to any disclaimer, the term of this patent is extended or adjusted under 35 U.S.C. 154(b) by 153 days.

(21) Appl. No.: 14/631,459

(22) Filed: Feb. 25, 2015

(65) Prior Publication Data

US 2015/0164306 A1    Jun. 18, 2015

Related U.S. Application Data

(63) Continuation of application No. 13/596,294, filed on Aug. 28, 2012, which is a continuation of application No. PCT/JP2012/053243, filed on Feb. 13, 2012.

(30) Foreign Application Priority Data

Feb. 28, 2011    (JP) ................. 2011-042551

(51) Int. Cl.
*A61B 1/005*    (2006.01)
*A61B 1/00*    (2006.01)
*G02B 23/24*    (2006.01)

(52) U.S. Cl.
CPC .......... *A61B 1/0057* (2013.01); *A61B 1/0016* (2013.01); *A61B 1/0052* (2013.01);
(Continued)

(58) Field of Classification Search
CPC ... A61B 1/0057; A61B 1/0053; A61B 1/0052; A61B 1/0051; A61B 1/005;
(Continued)

(56) References Cited

U.S. PATENT DOCUMENTS 3,913,568 A    10/1975 Carpenter
4,503,842 A *  3/1985 Takayama ............ A61B 1/0052
                                                200/6 A
(Continued)

FOREIGN PATENT DOCUMENTS

EP    2 671 499 A1    11/2013
EP    2 689 715 A1    1/2014
(Continued)

OTHER PUBLICATIONS

JPO Translation of the Description of JP 2009101076 A, Ogawa, May 14, 2009.*

(Continued)

*Primary Examiner* — Daniel D Yabut
(74) *Attorney, Agent, or Firm* — Scully, Scott, Murphy & Presser, P.C.

(57) ABSTRACT

A bending apparatus includes: a bending portion; an operation element erected vertically from an operation portion having a longitudinal axis and has a shaft portion in which a tilt direction and tilt angle are changeable; a pulling member having one end connected to the bending portion; a pulley on which a rotary body around which the pulling member is wound is arranged; a motor that generates a driving force that rotates the pulley to pull the pulling member wound around the rotary body in a winding direction; a hanging frame that extends in a diameter direction of the shaft portion, and includes an attachment portion to which the other end of the pulling member is attached; and an attachment path setting member provided inside the operation portion, which changes a path of the pulling to the longitudinal axis direction and guides the pulling member to the attachment portion.

8 Claims, 21 Drawing Sheets

(52) U.S. Cl.
CPC ...... *A61B 1/00066* (2013.01); *G02B 23/2476* (2013.01); *Y10T 74/18848* (2015.01); *Y10T 74/2042* (2015.01)

(58) Field of Classification Search
CPC  A61B 2017/00327; A61B 2017/00323; A61B 1/0016; A61B 1/00; A61B 34/71; A61B 2034/715; G02B 23/247; B25J 9/065; B25J 9/104; B25J 9/1045; B25J 9/1075; A61M 25/0147; A61M 25/0136; A61M 2025/015; Y10T 74/20323; Y10T 74/20329; Y10T 74/18848; Y10T 74/2042; Y10T 74/20486
See application file for complete search history.

(56) References Cited

U.S. PATENT DOCUMENTS

| | | |
|---|---|---|
| 4,688,555 A | 8/1987 | Wardle |
| 5,347,989 A | 9/1994 | Monroe et al. |
| 6,793,622 B2 | 9/2004 | Konomura et al. |
| 2003/0018237 A1* | 1/2003 | Okada ................ A61B 1/00039 600/146 |
| 2003/0092965 A1 | 5/2003 | Konomura et al. |
| 2008/0207998 A1 | 8/2008 | Maruyama |
| 2008/0275302 A1 | 11/2008 | Hosaka |
| 2010/0160730 A1* | 6/2010 | Konomura ......... G02B 23/2476 600/114 |
| 2010/0318100 A1 | 12/2010 | Okamoto et al. |

FOREIGN PATENT DOCUMENTS

| | | |
|---|---|---|
| EP | 2 805 664 A1 | 11/2014 |
| JP | 08224241 A | 9/1996 |
| JP | 2003325437 A | 11/2003 |
| JP | 2004321697 A | 11/2004 |
| JP | 2005013613 A | 1/2005 |
| JP | 2005102751 A | 4/2005 |
| JP | 2009005836 A | 1/2009 |
| JP | 2009101076 A | 5/2009 |
| JP | 2010207598 A | 9/2010 |

OTHER PUBLICATIONS

International Search Report dated Apr. 3, 2012 received in International Application No. PCT/JP2012/053243.
U.S. Non-Final Office Action dated Aug. 6, 2014 issued in related U.S. Appl. No. 13/596,294.
U.S. Final Office Action dated Nov. 28, 2014 issued in related U.S. Appl. No. 13/596,294.
Extended Supplementary European Search Report dated Dec. 19, 2017 in European Patent Application No. 12 75 2906.3.

* cited by examiner

BENDING APPARATUS

CROSS REFERENCE TO RELATED APPLICATION

This application is a continuation application of U.S. Ser. No. 13/596,294 filed on Aug. 28, 2012, which is a continuation application of PCT/JP2012/053243 filed on Feb. 13, 2012 and claims benefit of Japanese Application No. 2011-042551 filed in Japan on Feb. 28, 2011, the entire contents each of which are incorporated herein by reference.

BACKGROUND OF THE INVENTION

1. Field of the Invention

The present invention relates to a bending apparatus in which, by performing a tilt operation that changes a tilt direction and a tilt angle of an operation element provided in an operation portion, it is possible to move a pulling member and effect a bending operation of a bending portion provided in an insertion portion.

2. Description of the Related Art

In recent years, endoscopes that include an elongated insertion portion are being utilized in a medical field and an industrial field. Endoscopes utilized in the medical field are used to perform observation and the like by inserting the insertion portion into a body from an oral cavity or an anus or the like. Further, with an endoscope used in the industrial field, an observation can be conducted by inserting the insertion portion into a pipe of a boiler or inside an engine or the like.

In an endoscope, generally, in order to be able to point an observation optical system provided in a distal end portion of the insertion portion in a desired direction, a bending portion that bends, for example, in the vertical and lateral directions is provided on a distal end side of the insertion portion. A bending knob for effecting a bending operation of the bending portion is pivotably arranged in an operation portion that is provided at a proximal end of the insertion portion. An angle wire is connected at a predetermined position of the bending portion and at a predetermined position of the bending operation knob. In an endoscope configured in this manner, the configuration is such that when an operator rotates the bending operation knob clockwise or counterclockwise using fingers of a hand that is grasping the operation portion, the angle wire is pulled or slackened and the bending portion bends. (Hereunder, an endoscope having this configuration is referred to as a "conventional endoscope.")

In recent years, endoscopes have been proposed which have driving means that is provided inside an operation portion of the endoscope, and in which a bending operation of a bending portion can be effected by operating an operation element that is a bending mechanism with a single finger. For example, in FIG. 6 in Japanese Patent Application Laid-Open Publication No. 08-224241, an endoscope is illustrated in which a bending pipe is bent vertically and laterally by operating a joystick that is an operation element provided in a casing. According to this endoscope, when a surgeon subjects the joystick to a tilt operation, a controller converts the tilt operation into a bending angle in a vertical or lateral direction, and drives a driving actuator for vertical bending and/or a driving actuator for lateral bending. Thereupon, a wire is pulled/slackened by the driving force of the actuator and the bending portion performs a bending operation. Therefore, the surgeon can easily adjust the bending portion of the distal end portion.

However, in an endoscope in which a wire is pulled by a driving actuator, the wire is not directly pulled by the joystick that the surgeon operates. Consequently, a change does not occur in the operability of the joystick even if, during a bending operation of the bending portion, for example, the distal end portion contacts against living tissue and a load that is applied to the wire increases.

Japanese Patent Application Laid-Open Publication No. 2003-325437 discloses an endoscope that is equipped with a pulling member operation apparatus with which it is possible to effect a bending operation of a bending portion by tilting an operation instruction lever as an operation element using a slight amount of operation force thereby to directly move a desired pulling member by a desired amount. In this endoscope, by tilting a bending lever thereby to change a tension state of an operation wire that corresponds to the tilt operation direction that is fixed to an arm member, a drag between the operation wire and a pulley that is being rotated by a motor is changed. Thereupon, the operation wire is moved in the direction of rotation of the pulley and the bending portion bends. According to this endoscope, the relevant wire is directly pulled when a tilt operation of the bending lever is performed. As a result, operability is obtained such that, for example, when the distal end portion contacts against living tissue during a bending operation, the amount of tilt operation force increases along with an increase in a load that is applied to the relevant wire, and thus the above described problem can be solved.

In addition, Japanese Patent Application Laid-Open Publication No. 2010-207598 discloses an endoscope equipped with the pulling member operation apparatus described in Japanese Patent Application Laid-Open Publication No. 2003-325437. An operation portion of this endoscope includes an operation portion body, and a grasping portion that is provided on a side opposite to an insertion portion of the operation portion body so that an axis direction intersects with an insertion axis of the insertion portion and inclines downward relative to the insertion axis. When the grasping portion is grasped with the little finger, the ring finger, and the middle finger, a bending operation lever of this endoscope protrudes from a middle position on a front surface side of the operation portion body that is a position at which an operation can be performed with the thumb. Further, in this endoscope, a plurality of operation switches are disposed on a front surface side of the operation portion body on the grasping portion side that is in the vicinity of the bending operation lever.

SUMMARY OF THE INVENTION

According to one aspect of the present invention, a bending apparatus includes: a bending portion; a grasping portion that is included in an operation portion and has a longitudinal axis, and that is grasped when effecting a bending operation of the bending portion; an operation element that is erected vertically from the operation portion, and that has a shaft portion in which a tilt direction and a tilt angle are changeable; a pulling member having one end connected to the bending portion; a pulley that is disposed at a position that is deviated in the longitudinal axis direction relative to the operation element, and on which a rotary body around which an intermediate portion of the pulling member is wound is arranged in a loosely fitting state; a motor that is disposed at a position that is deviated in the longitudinal axis direction relative to the operation element, and that generates a driving force that rotates the pulley to pull the pulling member that is wound around the rotary body arranged on the pulley in a winding direction; a hanging frame that extends in a diameter direction of the shaft portion of the operation element, and that includes an attachment portion to which the other end of the pulling member that is wound around the rotary body is attached; and an attachment path setting member that is provided inside the operation portion and that leads the pulling member that is wound around the rotary body in the longitudinal axis direction, and changes a path of the pulling member that is led to a direction of a longitudinal axis of the shaft portion to guide the pulling member to the attachment portion.

BRIEF DESCRIPTION OF THE DRAWINGS

FIG. 1 to FIG. 5 relate to a first embodiment of the present invention, in which:

FIG. 1 is a view that illustrates an endoscope in which an operation element included in a pulling member operation apparatus is erected vertically in an operation portion;

FIG. 2 is a view that illustrates a configuration of a pulling member operation apparatus that contains a motor and a pulley in an operation portion that includes a grasping portion and an operation portion body;

FIG. 3 is a view that illustrates a rotary body;

FIG. 4 is a view that mainly illustrates a configuration of the motor and the pulley of the pulling member operation apparatus as viewed from an arrow Y4 direction in FIG. 2; and FIG. 5 is a view that mainly illustrates a configuration of an attachment path setting member and a hanging frame of the pulling member operation apparatus as viewed from the arrow Y4 direction in FIG. 2.

FIG. 6 to FIG. 9 relate to an application example of the present invention, in which:

FIG. 6 is a view that illustrates a pulling member operation apparatus that includes two pulleys that are arranged on two pulley shafts that are provided in a perpendicular positional relationship with respect to a motor shaft, and a driving force transmitting mechanism portion that transmits a driving force of the motor to the two pulleys;

FIG. 7 is a view that illustrates a relation between the two pulleys and a plurality of guide rollers as viewed from an arrow Y7 direction in FIG. 6;

FIG. 8 is a view that illustrates a different relation between a plurality of guide rollers, two pulleys, and rotary bodies; and FIG. 9 is a view that illustrates a relation between rotary bodies that are disposed on two pulleys and guide rollers as viewed from an arrow Y9 direction in FIG. 8.

FIG. 10 to FIG. 15 relate to a second embodiment of the present invention, in which:

FIG. 10 is a view that illustrates another configuration of a pulling member operation apparatus that contains a motor and a pulley in an operation portion that includes a grasping portion and an operation portion body;

FIG. 11 is a view that illustrates the pulling member operation apparatus as viewed from an arrow Y11 direction in FIG. 10;

FIG. 12 is a view that illustrates a configuration example of a second guide roller, a third guide roller, and a plurality of rotary bodies disposed on a pulley as viewed from the direction of a line indicated by arrows Y12-Y12 in FIG. 10;

FIG. 13 is a view that illustrates a configuration example of a plurality of second guide rollers, a plurality of third guide rollers, and a plurality of rotary bodies disposed on a pulley as viewed from the direction of a line indicated by arrows Y13-Y13 in FIG. 10, that is a modification example of the arrangement positions of guide rollers;

FIG. 14 is a view that illustrates a pulley having a configuration that includes a plurality of shaft bodies, that is a modification example of a pulley; and FIG. 15 is a view that illustrates the pulley as viewed from the direction of a line indicated by arrows Y15-Y15 in FIG. 14.

FIG. 16 to FIG. 24 relate to a third embodiment of the present invention, in which:

FIG. 16 is a view that illustrates an operation portion that includes a pulling member operation apparatus in which a motor having a motor shaft that is disposed so as to be orthogonal to a longitudinal axis of the operation portion, and a pulley having a pulley shaft that is disposed so as to be orthogonal to the longitudinal axis are contained in an operation portion body;

FIG. 17 is a view that illustrates the pulling member operation apparatus that is provided inside the operation portion body;

FIG. 18 is a perspective view that illustrates the configuration of the pulling member operation apparatus;

FIG. 19 is a top view of the pulling member operation apparatus illustrated in FIG. 18;

FIG. 20 is a side view of the pulling member operation apparatus illustrated in FIG. 18;

FIG. 21 is a top view of a pulling member operation apparatus in which the arrangement positions of the guide rollers are different;

FIG. 22 is a side view of the pulling member operation apparatus illustrated in FIG. 21;

FIG. 23 is a top view of a pulling member operation apparatus in which coil pipes are used as travel path changing members; and FIG. 24 is a side view of the pulling member operation apparatus shown in FIG. 23.

DETAILED DESCRIPTION OF THE PREFERRED EMBODIMENTS

Hereunder, embodiments of the present invention are described with reference to the drawings.

A first embodiment will now be described referring to FIG. 1 to FIG. 5.

Figure 1:
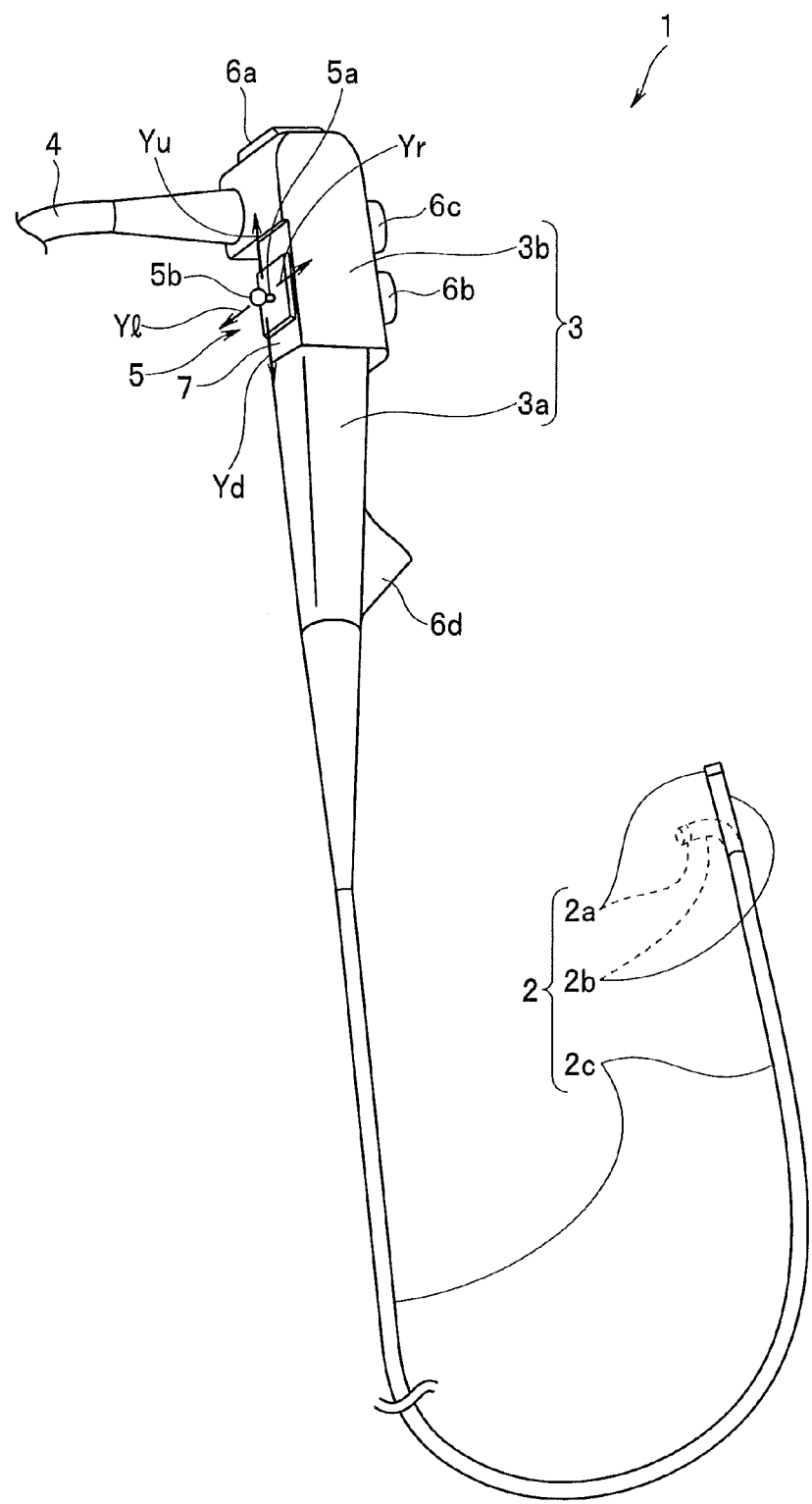

As shown in FIG. 1, an endoscope 1 of the present embodiment includes an elongated insertion portion 2, an operation portion 3 that is connected in series to a proximal end of the insertion portion 2, and a universal cord 4 that extends from a side portion of the operation portion 3.

The insertion portion 2 includes a distal end portion 2a, a bending portion 2b, and a flexible tube portion 2c that are connected in series in that order from the distal end side. An image pickup apparatus (unshown) that includes an image pickup device is contained inside the distal end portion 2a. The bending portion 2b is configured to be capable of bending in, for example, the vertical and lateral directions. The flexible tube portion 2c is long and has flexibility.

Figure 2:
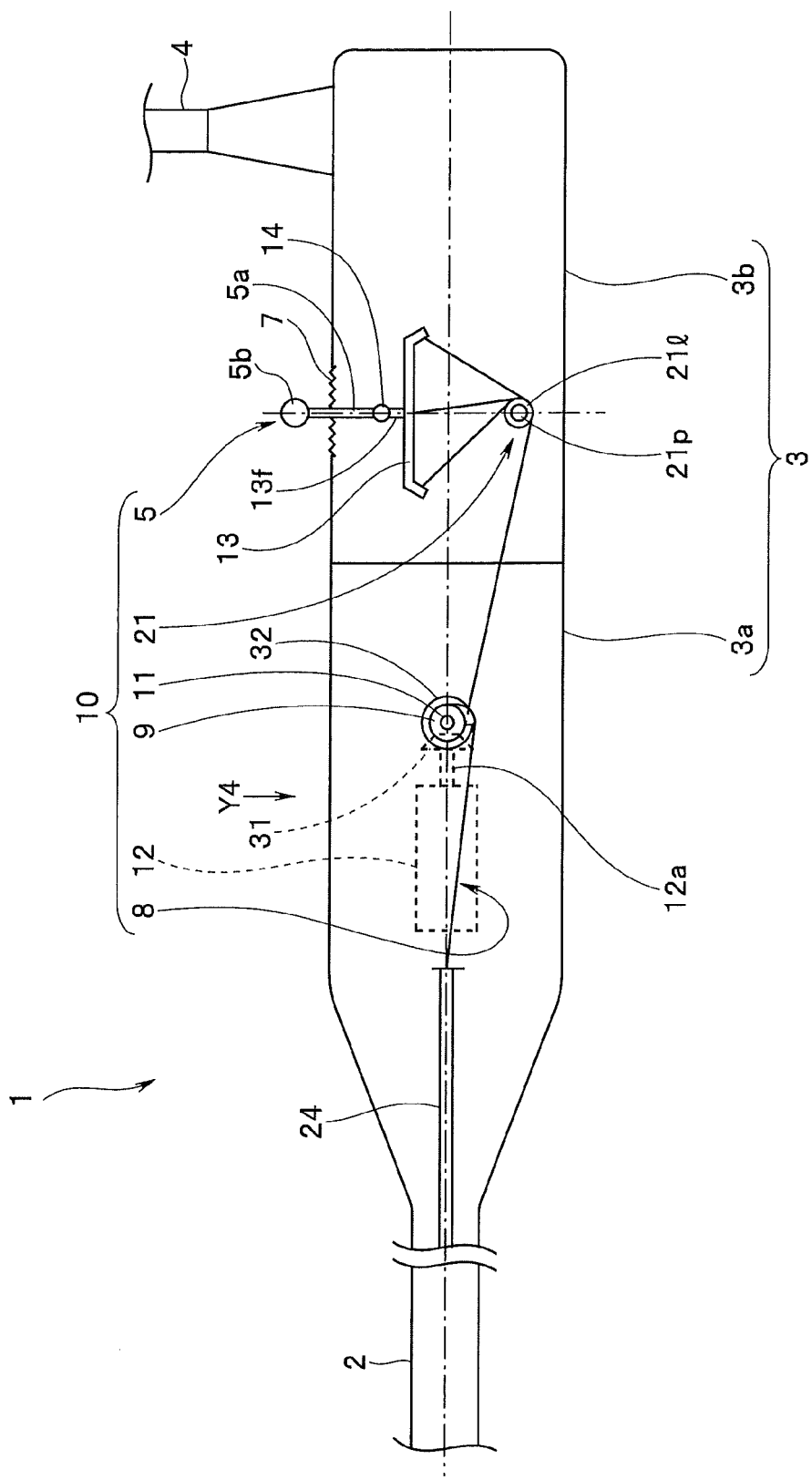

As shown in FIG. 1 and FIG. 2, the operation portion 3 includes a grasping portion 3a and an operation portion body 3b. The grasping portion 3a is connected in series to the insertion portion 2, and the operation portion body 3b is connected in series to the grasping portion 3a. The longitudinal axis of the grasping portion 3a and the insertion axis of the insertion portion 2 are in a coaxial or a parallel positional relationship with each other. An operation element 5 configured to cause the bending portion 2b to perform a bending operation is provided at a position corresponding to a portion at which the largest amount of vacant space exists on the distal end side of the operation portion body 3b. The longitudinal axis of the operation portion body 3b (also referred to as "longitudinal axis of the operation portion 3") and the longitudinal axis of the grasping portion 3a are in a coaxial or a parallel positional relationship with each other.

The operation element 5 is provided in a manner that intersects with the longitudinal axis of the operation portion 3 from an operation element protrusion port (unshown) that is an opening provided in one face of the operation portion body 3b.

The bending portion 2b is configured so as to bend in accordance with a tilt operation that includes a tilt direction and a tilt angle of the operation element 5, as shown by the arrows Yu, Yd, Yl, and Yr in FIG. 1. More specifically, in accordance with a tilting operation of the operation element 5, a bending operation wire (hereunder, abbreviated to "bending wire") that is described later is pulled/slackened and the bending portion 2b bends in the upward direction, the right direction, the downward direction, the left direction, a direction between the upward direction and the right direction, or the like.

In the present embodiment, the bending portion 2b is configured to bend in the four directions of upward, downward, left and right. However, the bending portion 2b may be configured to bend only in the upward and downward directions. The aforementioned reference characters "u," "d," "l" and "r" denote the upward, downward, left and right directions that are the bending directions of the bending portion 2b. In the following description, for example, reference symbol "8u" denotes a wire for upward bending, and reference symbol "9d" denotes a rotary body for the downward direction. Further, in the drawings, to distinguish the small letter "l" from the number "1", small letter "l" is shown in cursive style.

In this connection, as shown in FIG. 1, a switch 6a, an air/water supply button 6b, and a suction button 6c are provided at predetermined positions on the exterior of the operation portion body 3b, in addition to the operation element 5. The switch 6a is operated, for example, to input an instruction to perform various kinds of image pickup operations of the image pickup apparatus provided inside the distal end portion 2a. Further, a channel insertion port 6d that communicates with a treatment instrument channel (unshown) is provided on the exterior of the grasping portion 3a.

In the present embodiment, the operation element 5 is provided at a position at which the operation element 5 is operated by a thumb of the hand which grasps the operation portion 3 in a case where the operator grasps the grasping portion 3a of the operation portion 3 with the left hand in the same manner as for a conventional endoscope, the air/water supply button 6b and the suction button 6c are provided at positions at which the air/water supply button 6b and the suction button 6c are operated by fingers other than the thumb of the hand with which the operator grasps the operation portion 3, and the switch 6a is provided at a position at which the switch 6a can be operated by the thumb or another finger of the hand with which the operator grasps the operation portion 3.

Reference numeral 7 in FIG. 1 and FIG. 2 denotes a cover member. The cover member 7 blocks the operation element protrusion port in a watertight state, and adheres to a shaft portion 5a to retain the operation element 5 in a manner that enables a tilt operation thereof.

A signal cable, an electric wire, a light guide fiber bundle, an air supply tube, a water supply tube, a suction tube and the like are inserted through the inside of the universal cord 4. The signal cable is connected to the image pickup apparatus. The electric wire supplies electric power to a motor that is described later (see reference numeral 12 in FIG. 2). The light guide fiber bundle transmits illuminating light of a light source apparatus.

As shown in FIG. 2, a pulling member operation apparatus 10 is provided inside the operation portion 3. As shown in FIG. 2 to FIG. 5, the pulling member operation apparatus 10 is mainly constituted by four bending wires 8, an elongated pulley 11 on which four rotary bodies 9 are arranged, a motor 12 that is driving means, a substantially cruciform shaped hanging frame 13, the operation element 5, and a guide roller set 21 that includes a plurality of guide rollers that is described later. The bending wires 8 are pulling members. An intermediate portion of each wire 8 is wound around each rotary body 9, respectively. The motor 12 has a driving force that causes a predetermined rotary body 9 arranged on the pulley 11 to rotate with a predetermined torque at the time of a bending operation. The hanging frame 13 has wire attachment portions to which the proximal end portions of the respective wires 8 are respectively connected. The shaft portion 5a of the operation element 5 is integrally connected to the hanging frame 13. The plurality of guide rollers of the guide roller set 21 are wire travel path changing members that change a travel path of the four wires 8 inside the operation portion 3.

Figure 4:
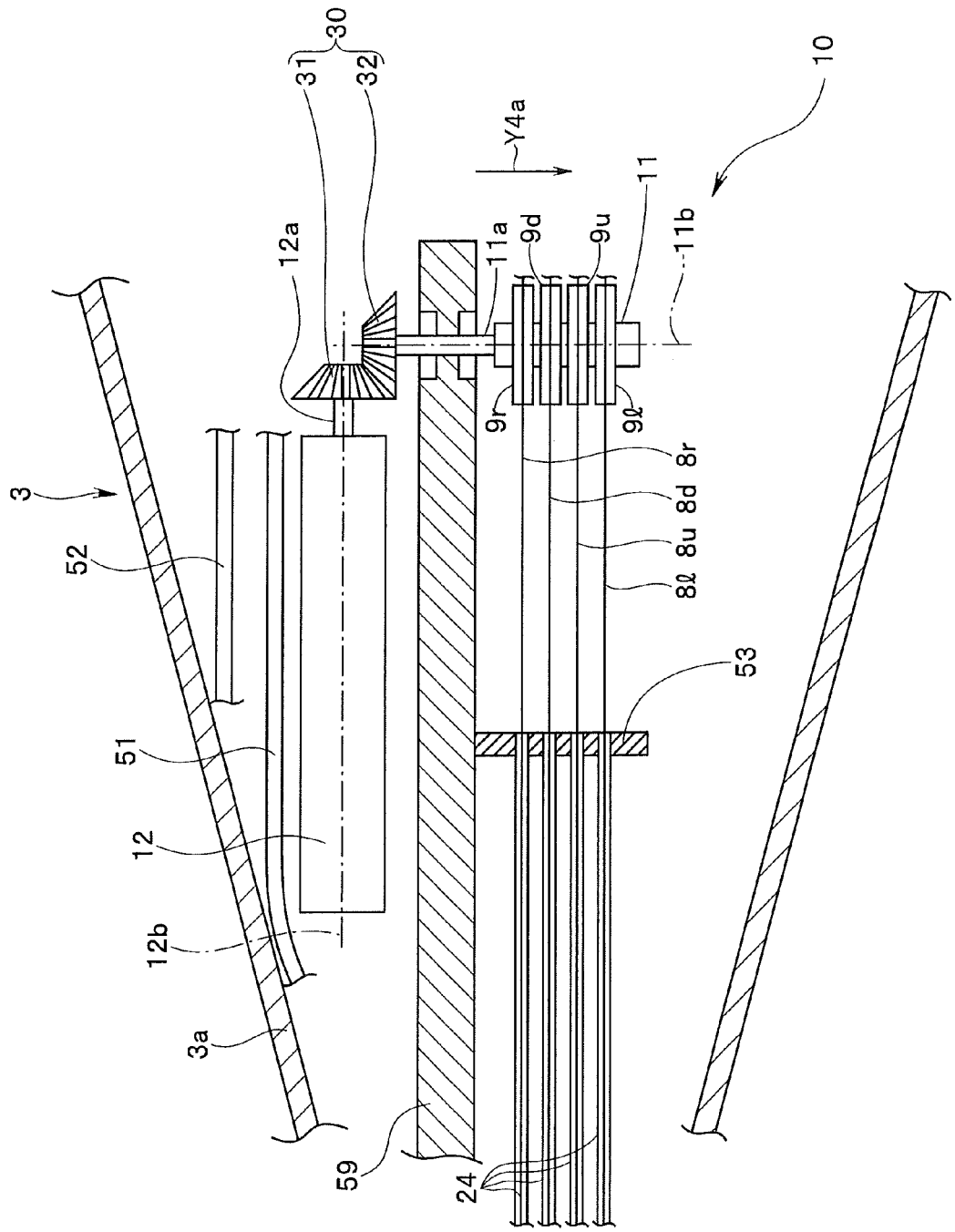

In FIG. 4, reference numeral 51 denotes a signal cable, reference numeral 52 denotes a light guide cable, reference numeral 53 denotes a coil pipe stopper, and reference numeral 59 denotes a partition plate. The present embodiment is configured so that the center of gravity of the operation portion 3 is positioned inside the grasping portion 3a.

The four bending wires 8 include a pair of a wire for upward bending (hereunder, referred to as "upward bending wire") 8u and a wire for downward bending (hereunder, referred to as "downward bending wire") 8d that are used for bending operations in the upward and downward directions, and a pair of a wire for left bending (hereunder, referred to as "left bending wire") 8l and a wire for right bending (hereunder, referred to as "right bending wire") 8r that are used for bending operations in the left and right directions.

In the present embodiment, the longitudinal axis of the pulley 11 and the longitudinal axis of the motor 12 intersect. More specifically, a drive shaft of the motor 12 is disposed at a predetermined position inside the grasping portion 3a so as to be in a parallel positional relationship with respect to the longitudinal axis of the grasping portion 3a. A motor shaft 12b of the motor 12 and a pulley shaft 11b that is a rotary shaft of the pulley 11 are set so as to be disposed in a perpendicular positional relationship with each other. The pulley 11 and the motor 12 are disposed in respectively different spaces inside the operation portion 3 that is partitioned by the partition plate 59, in a manner that interposes the partition plate 59 therebetween.

The configuration is such that a driving force of the motor 12 is transmitted to the pulley 11 by a driving force transmitting mechanism portion 30. The driving force transmitting mechanism portion 30 includes a first bevel gear 31 and a second bevel gear 32.

The first bevel gear 31 is integrally fixed to the shaft portion 12a of the motor 12. The second bevel gear 32 is integrally fixed to the shaft portion 11a of the pulley 11. According to this configuration, the pulley 11 is rotated around its axis when the driving force of the motor 12 is transmitted to the shaft portion 11a through the bevel gears 31 and 32.

Figure 3:
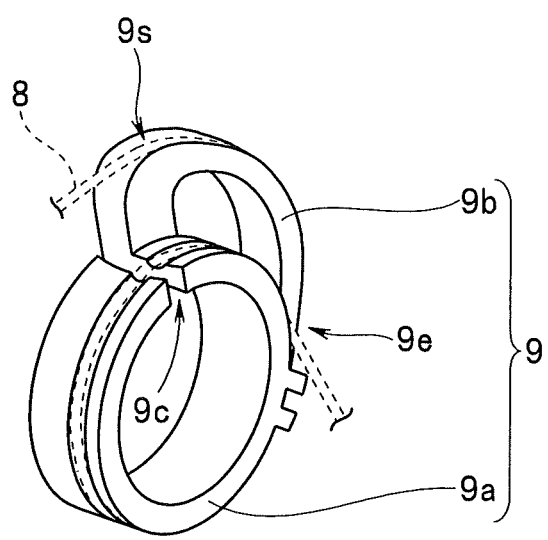

The rotary body 9 is elastically deformable. As shown in FIG. 3, the rotary body 9 includes, for example, an annular portion 9a and a rotation amount adjustment portion 9b. A gap 9c is formed in the annular portion 9a of the rotary body 9. An unshown wire guide portion is formed in the annular portion 9a and the rotation amount adjustment portion 9b. The wire guide portion is configured in a predetermined shape so as to smoothly guide the relevant wire 8 from a winding start position 9s to a winding end position 9e. Four rotary bodies 9u, 9d, 9l, and 9r are disposed in a predetermined loosely fitting state on the outer circumferential face of the pulley 11, and each of the rotary bodies 9u, 9d, 9l, and 9r rotates independently.

Figure 5:
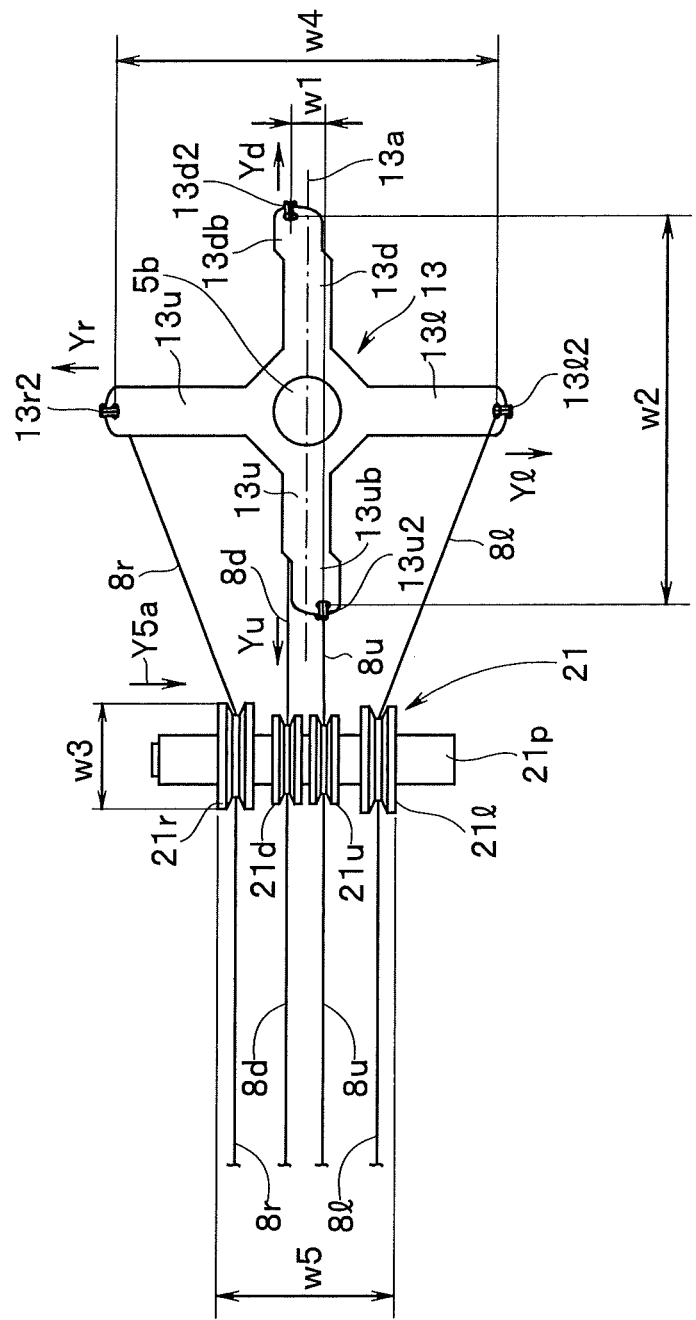

The hanging frame 13 shown in FIG. 5 is disposed so as to be in a predetermined positional relationship within a vacant space on the distal end side of the operation portion body 3b shown in FIG. 2.

As shown in FIG. 5, the hanging frame 13 includes four frames 13u, 13d, 13l, and 13r, and is formed in a substantially cruciform shape. A frame for an upward direction (hereunder, referred to as "upward frame") 13u and a frame for a downward direction (hereunder, referred to as "downward frame") 13d that correspond to the pair of bending wires 8u and 8d are collinearly disposed in a manner that interposes the shaft portion 5a therebetween. An upward wire attachment portion 13u2 is provided at an end portion of the upward frame 13u, and a downward wire attachment portion 13d2 is provided at an end portion of the downward frame 13d.

In addition, a frame for a left direction (hereunder, referred to as "left frame") 13l and a frame for a right direction (hereunder, referred to as "right frame") 13r that correspond to the pair of bending wires 8l and 8r are collinearly disposed in a perpendicular manner with respect to an upward/downward frame center line (hereunder, referred to as "frame center line") 13a in a manner that interposes the shaft portion 5a therebetween. A left wire attachment portion 13l2 is provided at an end portion of the left frame 13l, and a right wire attachment portion 13r2 is provided at an end portion of the right frame 13r.

The upward frame 13u includes, at an end portion thereof, an upward frame distal end curved portion 13ub that is curved in one direction relative to the frame center line 13a. The downward frame 13d includes, at an end portion thereof, a downward frame distal end curved portion 13db that is curved in one direction relative to the frame center line 13a.

The upward wire attachment portion 13u2 is provided in the upward frame distal end curved portion 13ub, and the downward wire attachment portion 13d2 is provided in the downward frame distal end curved portion 13db. As a result, an interval w1 in a direction that is orthogonal to the longitudinal axis of the operation portion 3 between the upward wire attachment portion 13u2 and the downward wire attachment portion 13d2 is set to a predetermined size.

In this connection, the upward frame 13u and the upward wire attachment portion 13u2 and the like are components that are set by taking into consideration the tilt directions of the operation element 5 and the bending directions of the bending portion 2b. According to the present embodiment, a configuration is adopted such that when the operation element 5 is tilted in the arrow Yu direction in FIG. 1, the upward wire attachment portion 13u2 sways and is tilted in the arrow Yu direction in FIG. 5 and the bending portion 2b bends in the upward direction. Similarly, when the operation element 5 is tilted in the arrow Yd direction in FIG. 1, the downward wire attachment portion 13d2 sways and is tilted in the arrow Yd direction in FIG. 5 and the bending portion 2b bends in the downward direction. Further, when the operation element 5 is tilted in the arrow Yl direction in FIG. 1, the left wire attachment portion 13l2 sways and is tilted in the arrow Yl direction in FIG. 5 and the bending portion 2b bends in the left direction. Similarly, when the operation element 5 is tilted in the arrow Yr direction in FIG. 1, the right wire attachment portion 13r2 sways and is tilted in the arrow Yr direction in FIG. 5 and the bending portion 2b bends in the right direction.

In the present embodiment, the hanging frame 13 is disposed at a predetermined position inside the operation portion 3 so that the frame center line 13a and the longitudinal axis of the grasping portion 3a are parallel.

As shown in FIG. 2 and FIG. 5, the guide roller set 21 includes a roller shaft 21p and four guide rollers 21u, 21d, 21l, and 21r. The roller shaft 21p is a support body that is, for example, a cylindrical shape. The four guide rollers 21u, 21d, 21l, and 21r are pivotably disposed on the roller shaft 21p.

The four guide rollers 21u, 21d, 21l, and 21r correspond to the four bending wires 8u, 8d, 8l, and 8r, respectively. The four guide rollers 21u, 21d, 21l, and 21r are provided at positions that are separated by a predetermined distance from the pulley 11 and the hanging frame 13. The four guide rollers 21u, 21d, 21l and 21r are attachment path setting members that guide the four bending wires 8u, 8d, 8l, and 8r to the wire attachment portions 13u2, 13d2, 13l2, and 13r2 of the hanging frame 13.

The roller shaft 21p is disposed at a predetermined position directly below the shaft portion 5a, in an intersecting positional relationship with respect to the longitudinal axis of the grasping portion 3a. The center of the roller shaft 21p is positioned on the central axis of the shaft portion 5a in an upright state.

The respective bending wires 8u, 8d, 8l and 8r are configured so as to arrive at the upward wire attachment portion 13u2, the downward wire attachment portion 13d2, the left wire attachment portion 13l2 and the right wire attachment portion 13r2 of the hanging frame 13, respectively, after the respective travel paths of the bending wires 8u, 8d, 8l and 8r have been changed by the guide rollers 21u, 21d, 21l and 21r.

The guide rollers 21 will now be described referring to FIG. 5.

In this connection, in FIG. 5, in order to describe the positional relation between the respective bending wires 8u, 8d, 8l and 8r and the respective wire attachment portions 13u2, 13d2, 13l2 and 13r2, the position of the hanging frame 13 is displaced in the right direction in the drawing with respect to the roller shaft 21p.

As shown in FIG. 5, the four guide rollers 21u, 21d, 21l and 21r are disposed in the order of guide rollers 21r, 21d, 21u and 21l as shown by the arrow Y5a in FIG. 5 with respect to the roller shaft 21p.

There is a difference in the diametrical dimensions or width dimensions between the guide rollers 21r and 21l disposed at the two ends of the roller shaft 21p and the guide rollers 21u and 21d disposed on the inner side of the guide rollers 21r and 21l in a manner that interposes the center of the roller shaft 21p therebetween. At least the width dimensions of the guide rollers 21l and 21r are set so as to be wider than the width dimensions of the guide rollers 21u and 21d.

When the maximum external diameter of the guide rollers 21l, 21r, 21u and 21d is taken as w3 and an interval in the longitudinal axis direction of the operation portion 3 between the upward wire attachment portion 13u2 and the downward wire attachment portion 13d2 is taken as w2, the relation w2>w3 is set with respect to the interval w2 and the maximum external diameter w3.

Further, an interval between the center of the guide roller 21u and the center of the guide roller 21d is set to an interval w1 that is an interval between the upward wire attachment portion 13u2 and the downward wire attachment portion 13d2.

In addition, a relation w4>w5 is set with respect to an interval w4 between the left wire attachment portion 13l2 and the right wire attachment portion 13r2, and an interval w5 between an outer end of the left guide roller 21l disposed on the roller shaft 21p and an outer end of the right guide roller 21r disposed on the roller shaft 21p.

The four rotary bodies 9 disposed on the pulley 11 are disposed in the order of rotary bodies 9r, 9d, 9u and 9l as shown by the arrow Y4a in FIG. 4.

The travel paths inside the operation portion 3 of the respective bending wires 8u, 8d, 8l and 8r will now be described referring to FIG. 2, FIG. 4 and FIG. 5.

As shown in FIG. 5, the respective proximal end portions of the four bending wires 8u, 8d, 8l and 8r are fixed to the wire attachment portions 13u2, 13d2, 13l2 and 13r2 that are at predetermined positions of the hanging frame 13.

On the other hand, the respective distal end portions of the bending wires 8u, 8d, 8l and 8r are fixed at positions corresponding to up, down, left and right of unshown distal end bending pieces that are included in the bending portion 2b. The distal end bending pieces are bending pieces that constitute the most distal end of a bending portion set that is configured so as to bend in the vertical and lateral directions, in which a plurality of unshown bending pieces included in the bending portion 2b are connected in series.

The respective bending wires 8u, 8d, 8l and 8r are inserted so as to freely advance and retract inside guides 24 that are formed, for example, with coil pipes made of metal that have through-holes that correspond to the wires 8u, 8d, 8l and 8r inside the insertion portion 2, respectively.

As shown in FIG. 2, FIG. 4 and FIG. 5, the respective bending wires 8u, 8d, 8l and 8r that are fixed to the distal end bending pieces extend inside the operation portion 3 through the guides 24.

The respective bending wires 8u, 8d, 8l and 8r are wound around the rotary bodies 9u, 9d, 9l and 9r disposed on the pulley 11, respectively. More specifically, each of the bending wires 8u, 8d, 8l and 8r are wound around the rotary bodies 9u, 9d, 9l and 9r so as to be in a predetermined slackened state from the respective winding start positions 9s of the corresponding rotary body 9u, 9d, 9l or 9r. Thereafter, the respective bending wires 8u, 8d, 8l and 8r are led towards the respective guide rollers 21u, 21d, 21l and 21r from the respective winding end positions 9e of the rotary bodies 9u, 9d, 9l and 9r.

The respective bending wires 8u, 8d, 8l and 8r that are led from the respective rotary bodies 9u, 9d, 9l and 9r are guided to the respective guide rollers 21u, 21d, 21l and 21r, and the wire travel paths are changed thereby so that the bending wires 8u, 8d, 8l and 8r are guided to the wire attachment portions 13u2, 13d2, 13l2 and 13r2 provided in the hanging frame 13. The respective proximal end portions of the bending wires 8u, 8d, 8l and 8r are fixed to the wire attachment portions 13u2, 13d2, 13l2 and 13r2.

As described above, the width dimensions of the guide rollers 21l and 21r are set so as to be wider than the width dimensions of the guide rollers 21u and 21d, and the interval w4 is set so as to be greater than the interval w5. As a result, the bending wires 8l and 8r pass smoothly through the guide rollers 21l and 21r and are guided to the wire attachment portions 13l2 and 13r2.

In this connection, the shaft portion 5a of the operation element 5 and a frame convex portion 13f that is a central shaft of the hanging frame 13 are coaxially mounted and fixed through a pivotably arranged universal joint 14 to an unshown frame. When the shaft portion 5a of the operation element 5 is in an upright state as shown in FIG. 2, the respective bending wires 8u, 8d, 8l and 8r that extend from the guide rollers 21u, 21d, 21l and 21r towards the hanging frame 13 are all in a predetermined slackened state.

Reference symbol 5b denotes a finger contact portion that is a spherical shape. The finger contact portion 5b is integrally fixed to a distal end of the shaft portion 5a.

A configuration may also be adopted in which a partition member is provided between adjacent bending wires 8, to thereby prevent the bending wires 8 from tangling together.

Thus, in the configuration in which the pulley 11 and the motor 12 are disposed inside the operation portion 3 having a longitudinal axis that is parallel to the longitudinal axis of the insertion portion 2 included in the endoscope 1, the motor shaft 12b of the motor 12 is disposed parallel to the longitudinal axis of the grasping portion 3a, and the pulley shaft 11b of the pulley 11 is made orthogonal to the motor shaft 12b of the motor 12.

In addition, the guide roller set 21 having the roller shaft 21p that intersects at right angles with the longitudinal axis of the operation portion 3, in other words, that is parallel to the pulley shaft 11b, is disposed at a predetermined position as a wire travel path changing member.

Further, the respective bending wires 8u, 8d, 8l and 8r that are led inside the operation portion 3 and travel towards the proximal end side of the operation portion 3 are wound around the respective rotary bodies 9u, 9d, 9l and 9r disposed on the pulley 11 from the respective winding start positions 9s. The respective bending wires 8u, 8d, 8l and 8r are wound around the respective rotary bodies 9u, 9d, 9l and 9r in a slackened state and led out from the respective winding end positions. The bending wires 8u, 8d, 8l and 8r that are led out are guided towards the guide rollers 21u, 21d, 21l and 21r. Thereafter, the travel path of the bending wires 8u, 8d, 8l and 8r is changed by the guide rollers 21u, 21d, 21l and 21r, respectively, and the bending wires 8u, 8d, 8l and 8r are led to the wire attachment portions 13u2, 13d2, 13l2 and 13r2 of the hanging frame 13 and fixed thereto.

According to the endoscope 1 configured in the above manner, in a state in which the motor 12 is driven and the pulley 11 is rotated, when the shaft portion 5a of the operation element 5 is in an upright state each of the bending wires 8u, 8d, 8l and 8r that are wound around the rotary bodies 9u, 9d, 9l and 9r disposed on the pulley 11, respectively, enters a predetermined slackened state. As a result, all of the rotary bodies 9u, 9d, 9l and 9r enter a sliding state with respect to the pulley 11, and the bending portion 2b is maintained in a straight state.

On the other hand, in a state in which the operator has grasped the grasping portion 3a, to cause the bending portion 2b to perform a bending operation in, for example, the upward direction, the operator places the ball of the thumb on the finger contact portion 5b of the operation element 5 and tilts the shaft portion 5a in the direction of the arrow Yu in FIG. 1. Thereupon, accompanying the operation to tilt the operation element 5, the hanging frame 13 inclines, and the upward bending wire 8u fixed to the upward wire attachment portion 13u2 gradually changes from a slackened state to a tensed state. In contrast, the other bending wires 8d, 8l and 8r change to a state in which the bending wires 8d, 8l and 8r are more slackened.

Accordingly, among the respective bending wires 8u, 8d, 8l and 8r that were wound in a slackened state around the respective rotary bodies 9u, 9d, 9l and 9r of the pulley 11, only the upward bending wire 8u is pulled. Thereupon, the gap 9c in a rotary body for upward bending (hereunder, referred to as "upward rotary body") 9u is narrowed in resistance to an elastic force and is thus contracted, and the state changes to one in which the upward rotary body 9u and the pulley 11 are in a closely contacting state. Consequently, frictional resistance arises between the upward rotary body 9u and the pulley 11, and the upward rotary body 9u is rotated while sliding with respect to the pulley 11 in the same direction as the pulley 11. As a result, the upward bending wire 8u that is disposed further on the insertion portion 2 side than the upward rotary body 9u is pulled and moved accompanying rotation of the upward rotary body 9u, and the bending portion 2b starts a bending movement in the upward direction.

In this case, if the operator continues the operation to tilt the shaft portion 5a in the same direction so as to cause the upward rotary body 9u to closely contact the pulley 11, the upward rotary body 9u that is in the closely contacting state is brought into even closer contact with the pulley 11 and the frictional force increases. As a result, the wire for upward bending 8u that is disposed at a position that is further on the insertion portion 2 side than the upward rotary body 9u is pulled and moved to a further degree accompanying rotation of the rotary body 9u, and thus the bending portion 2b bends further in the upward direction.

In contrast, if the operator continues to maintain the tilt position of the operation element 5, the tightness between the upward rotary body 9u and the pulley 11 is maintained. Thus, movement stops in a state in which a tensile force has arisen at the upward bending wire 8u disposed at a position that is further on the distal end side than the upward rotary body 9u.

At this time, each of the bending wires 8d, 8l and 8r is in a slackened state. Accordingly, by continuing to retain the operation element 5 in this tilt operation state, the tensed state of the upward bending wire 8u and the slackened states of the bending wires 8d, 8l and 8r are retained, respectively, and the bending portion 2b is maintained in a bent state that corresponds to the tilt operation.

Subsequently, the operator performs a tilt operation with respect to the operation element 5 to bend the bending portion 2b further in the same direction, to bend the bending portion 2b in another direction, or to return the bending portion 2b to the original state thereof. Thereupon, the bending wires 8u, 8d, 8l and 8r are pulled or slackened in accordance with the tilt operation, a change arises in the loosely fitting state or the closely contacting state of the pulley 11 and the rotary bodies 9 that correspond to the bending wires 8, and the bending portion 2b changes to a state that corresponds to the tilt operation of the operation element 5.

According to this configuration, the end portions of the respective bending wires 8u, 8d, 8l and 8r are fixed to the wire attachment portions 13u2, 13d2, 13l2 and 13r2 of the hanging frame 13 that is fixed to the shaft portion 5a of the operation element 5, by using the guide roller set 21 to change the wire travel paths of the respective bending wires 8u, 8d, 8l and 8r that are led inside the operation portion 3. As a result, the respective bending wires 8u, 8d, 8l and 8r can be smoothly pulled or slackened by a tilt operation of the operation element 5.

Further, in a state in which the operator has grasped the operation portion 3, that is, during endoscopy, the operator can easily operate not just the operation element 5, but also the air/water supply button 6b, the suction button 6c and the switch 6a.

An application example of the present invention will now be described referring to FIG. 6 to FIG. 9.

Figure 6:
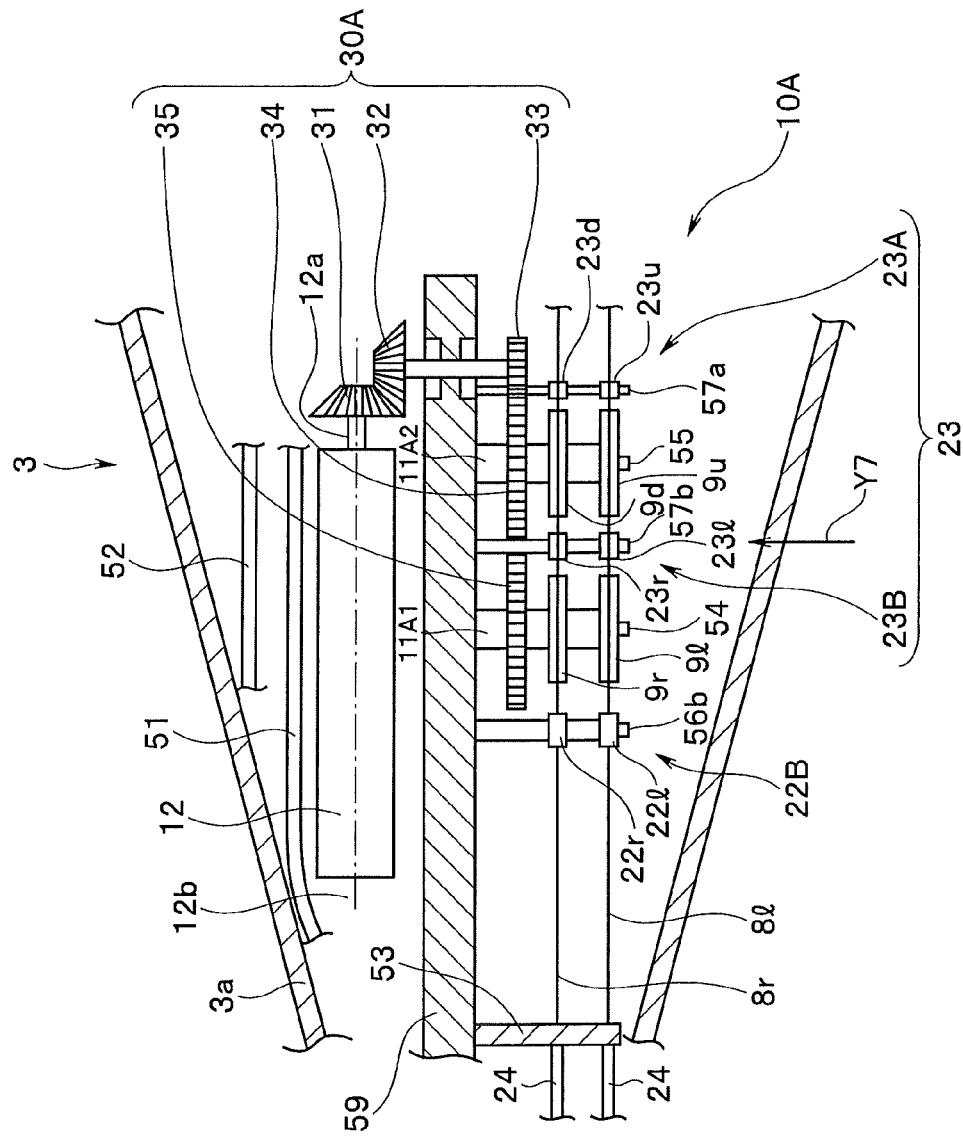
Figure 7:
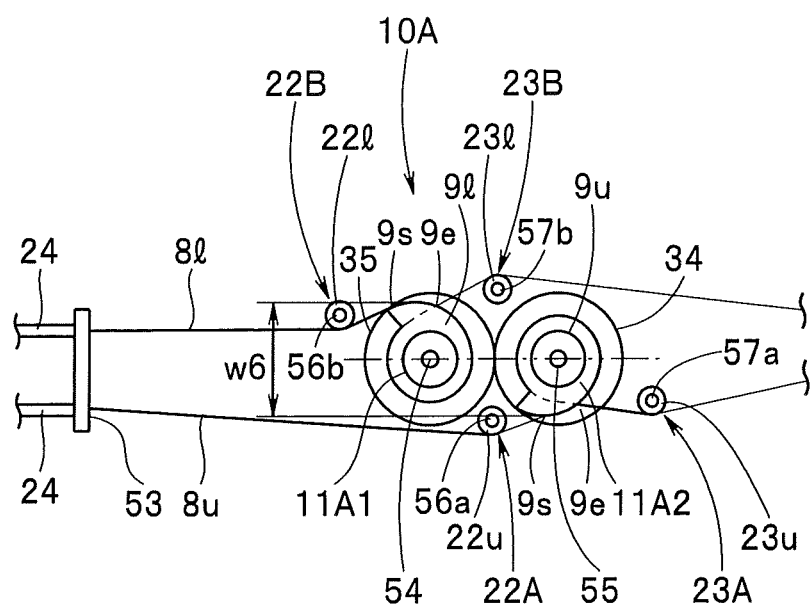
Figure 8:
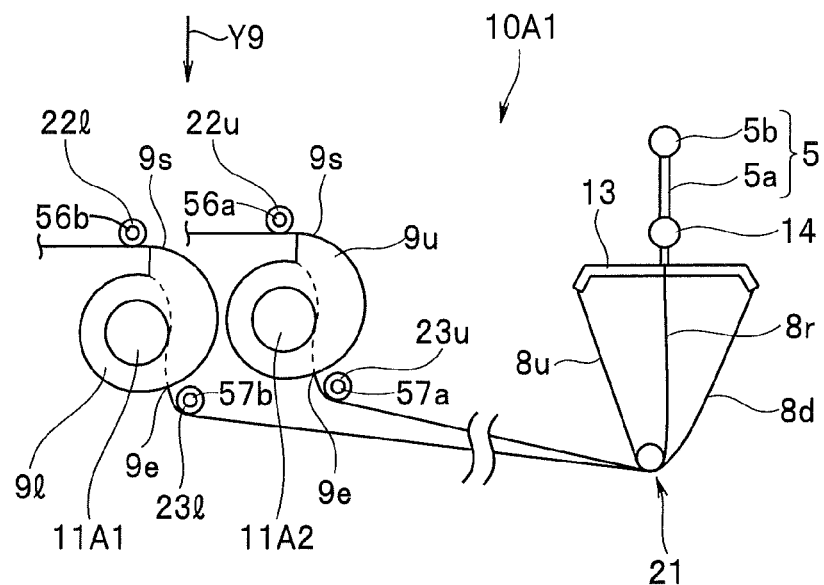
Figure 9:
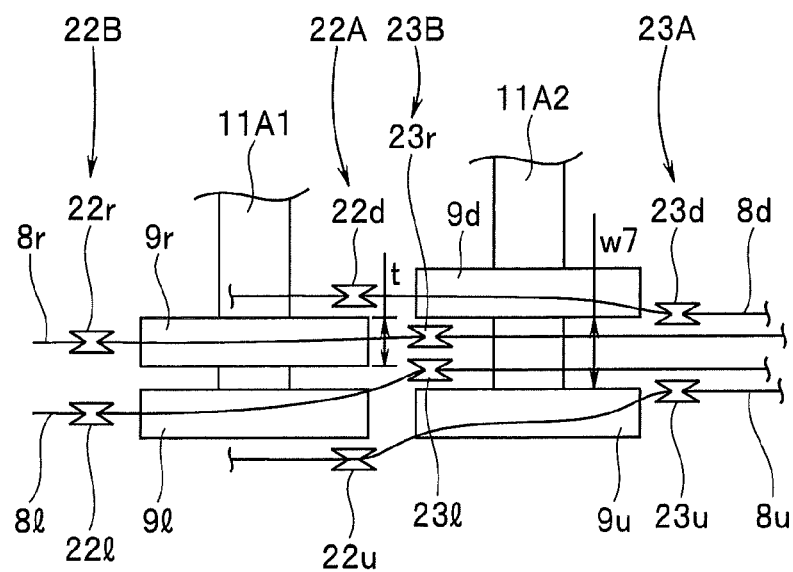

FIG. 6 is a view that illustrates the configuration of a pulling member operation apparatus including pulleys that are provided in a perpendicular positional relationship with respect to a motor shaft. FIG. 7 is a view that illustrates a relation between a plurality of guide rollers, two pulleys, and rotary bodies as viewed from an arrow Y7 direction in FIG. 6. FIG. 8 is a view that illustrates a different relation between a plurality of guide rollers, two pulleys, and rotary bodies. FIG. 9 is a view that illustrates guide rollers and rotary bodies as viewed from an arrow Y9 direction in FIG. 8.

As shown in FIG. 6 and FIG. 7, a pulling member operation apparatus 10A of the present embodiment includes two pulleys 11A1 and 11A2, a driving force transmitting mechanism portion 30A, the four bending wires 8, the four rotary bodies 9, the motor 12, the hanging frame 13 (not shown in FIG. 6 and FIG. 7) and the operation element 5 (not shown in FIG. 6 and FIG. 7) that are described above, and a plurality of guide roller sets 21, 22 and 23. The first pulley 11A1 and the second pulley 11A2 are disposed at predetermined positions in a parallel positional relationship with each other. The travel paths of the respective bending wires 8u, 8d, 8l and 8r are changed by the plurality of guide roller sets 21, 22 and 23. The plurality of guide roller sets 21, 22 and 23 each include wire travel path changing members.

In this connection, a first guide roller set 21 is an attachment member that includes the above described guide rollers 21u, 21d, 21l and 21r as first wire travel path changing members, and is not shown in FIG. 6 and FIG. 7. A second guide roller set 22 includes second guide rollers 22u, 22d, 22l and 22r, described later, as second wire travel path changing members. A third guide roller set 23 includes third guide rollers 23u, 23d, 23l and 23r, described later, as third wire travel path changing members.

In the present embodiment, the guide rollers 21u, 21d, 21l and 21r are the first guide rollers 21u, 21d, 21l and 21r.

Reference numerals 54 and 55 denote pulley shafts, and reference numerals 56a, 56b, 57a and 57b denote roller shafts.

In the present embodiment also, a configuration is adopted so that the center of gravity of the operation portion 3 is positioned inside the grasping portion 3a.

In the present embodiment, the first pulley 11A1 is pivotably attached to a first pulley shaft 54 that is provided orthogonal to the longitudinal axis of the grasping portion 3a that is fixed to the partition plate 59. The second pulley 11A2 is pivotably attached to a second pulley shaft 55 that is provided orthogonal to the longitudinal axis of the grasping portion 3a that is fixed to the partition plate 59. Accordingly, in the present embodiment, the motor shaft 12b of the motor 12 and the pulley shafts 54 and 55 are set in a perpendicular positional relationship with each other. Further, the configuration is such that the driving force of the motor 12 is transmitted to the pulleys 11A1 and 11A2 by the driving force transmitting mechanism portion 30A.

The driving force transmitting mechanism portion 30A is a gear train, and in addition to the first bevel gear 31 and the second bevel gear 32, includes a first spur gear 33, a second spur gear 34, and a third spur gear 35. The first bevel gear 31 is fixed to the shaft portion 12a of the motor 12. The second bevel gear 32 and the first spur gear 33 are fixed to predetermined positions of a gear shaft 36 that is pivotably supported by the partition plate 59. The second bevel gear 32 is fixed to an end portion of the gear shaft 36, and intermeshes with the first bevel gear 31. The first spur gear 33 is fixed to a predetermined position on the other end portion side of the gear shaft 36. The second spur gear 34 is fixed to the second pulley 11B, and intermeshes with the first spur gear 33. The third spur gear 35 is fixed to the first pulley 11A, and intermeshes with the second spur gear 34.

According to this configuration, similarly to the above described configuration, the single motor 12 and the two pulleys 11A1 and 11A2 can be disposed in different spaces inside the operation portion 3, in manner that interposes the partition plate 59 therebetween.

Further, when the motor 12 enters a driving state, rotation of the shaft portion 12a of the motor 12 is transmitted to the first bevel gear 31, the second bevel gear 32, the gear shaft 36, the first spur gear 33, the second spur gear 34 and the third spur gear 35, and thus the first pulley 11A1 and the second pulley 11A2 rotate in different directions. More specifically, the first pulley 11A1 shown in FIG. 7 rotates clockwise, and the second pulley 11A2 shown in FIG. 7 rotates counterclockwise.

As shown in FIG. 6, for example, a rotary body for the left direction (hereunder, referred to as "left rotary body") 9l and a rotary body for the right direction (hereunder, referred to as "right rotary body") 9r are disposed at predetermined positions with a predetermined interval therebetween on the first pulley 11A1. Further, for example, the upward rotary body 9u and a rotary body for the downward direction (hereunder, referred to as "downward rotary body") 9d are disposed at predetermined positions on the second pulley 11A2 with an interval therebetween that is the same as the interval between the left rotary body 9l and the right rotary body 9r.

As shown in FIG. 7, the winding start position 9s of the left rotary body 9l and the winding start position 9s of the right rotary body 9r that are disposed on the first pulley 11A1 are set on the upper side in the drawing. In contrast, the winding start position 9s of the upward rotary body 9u and the winding start position 9s of the downward rotary body 9d that are disposed on the second pulley 11A2 are set on the lower side in the drawing. Consequently, the winding direction of the bending wires 8u and 8d and the winding direction of the bending wires 8l and 8r are opposite directions to each other.

As shown in FIG. 6 and FIG. 7, the second guide roller set 22 includes a second guide roller set for the upward/downward directions (hereunder, referred to as "second upward/downward guide roller set") 22A, and a second guide roller set for the left/right directions (hereunder, referred to as "second left/right guide roller set") 22B. The second upward/downward guide roller set 22A includes a second roller shaft for the upward/downward directions (hereunder, referred to as "second upward/downward roller shaft") 56a as one first support body, and the second guide rollers 22u and 22d. The second guide rollers 22u and 22d are pivotably disposed on the second upward/downward roller shaft 56a, respectively.

The second left/right guide roller set 22B includes a second roller shaft for the left/right directions 56b as the other first support body, and the second guide rollers 22l and 22r. The second guide rollers 22l and 22r are pivotably disposed on the second roller shaft for the left/right directions 56b, respectively.

The second guide rollers 22u and 22d of the second upward/downward guide roller set 22A are disposed so as to correspond to the winding start positions 9s that are set on the lower side in the drawings of the upward rotary body 9u and the downward rotary body 9d that are disposed on the second pulley 11A2. Further, the second guide rollers 22l and 22r of the second left/right guide roller set 22B are disposed so as to correspond to the winding start positions 9s that are set on the upper side in the drawings of the left rotary body 9l and the right rotary body 9r that are disposed on the first pulley 11A1.

In the present embodiment, the respective second guide rollers 22u, 22d, 22l and 22r are pulley lead-in members that guide the respective bending wires 8u, 8d, 8l and 8r to the pulleys 11A1 and 11A2.

The third guide roller set 23 includes a third guide roller set for the upward/downward directions (hereunder, referred to as "third upward/downward guide roller set") 23A and a third guide roller set for the left/right directions (hereunder, referred to as "third left/right guide roller set") 23B. The third upward/downward guide roller set 23A includes a third roller shaft for the upward/downward directions 57a as one second support body, and the third guide rollers 23u and 23d. The third guide rollers 23u and 23d are pivotably disposed on the third roller shaft for the upward/downward directions 57a.

The third left/right guide roller set 23B includes a third roller shaft for the left/right directions 57b as the other second support body, and the third guide rollers 23l and 23r. The third guide rollers 23l and 23r are pivotably disposed on the third roller shaft for the left/right directions 57b.

The third guide rollers 23u and 23d of the third upward/downward guide roller set 23A are disposed so as to correspond to the winding end positions 9e that are set on the lower side in the drawings of the upward rotary body 9u and the downward rotary body 9d that are disposed on the second pulley 11A2. Further, the third guide rollers 23l and 23r of the third left/right guide roller set 23B are disposed so as to correspond to the winding end positions 9e that are set on the upper side in the drawings of the left rotary body 9l and the right rotary body 9r that are disposed on the first pulley 11A1.

In the present embodiment, the respective third guide rollers 23u, 23d, 23l and 23r are pulley lead-out members that guide the respective bending wires 8u, 8d, 8l and 8r from the pulleys 11A1 and 11A2 towards a desired direction.

The second guide rollers 22u and 22d that correspond to the bending wires 8u and 8d and the third guide rollers 23l and 23r that correspond to the bending wires 8l and 8r are disposed at predetermined positions in a positional relationship such that the second guide rollers 22u and 22d and the third guide rollers 23l and 23r are facing in a manner that interposes therebetween a hypothetical line (see the chain double-dashed line in FIG. 7) that links together the centers of the pulley shafts 54 and 55 that are disposed in parallel.

Further, a distance w6 between the winding start positions 9s of the rotary bodies 9u and 9d and the winding start positions 9s of the rotary bodies 9l and 9r is configured so that the winding start positions 9s of the rotary bodies 9u and 9d and the winding start positions 9s of the rotary bodies 9l and 9r are separated by a maximum distance amount of the rotary bodies 9.

As shown in FIG. 6, the second guide roller 22r, the right rotary body 9r, and the third guide roller 23r are disposed in a straight line, and the second guide roller 21d, the downward rotary body 9d, and the third guide roller 23d are disposed in a straight line. Likewise, the second guide roller 22l, the left rotary body 9l, and the third guide roller 23l are disposed in a straight line, and the second guide roller 22u, the upward rotary body 9u, and the third guide roller 23u are disposed in a straight line.

Thus, entanglement between the respective bending wires 8u, 8d, 8l and 8r is prevented.

According to the above described configuration, the bending wires 8u and 8d are extended to the lower side in FIG. 7 that is one side inside the operation portion 3 through the guides 24, and guided to the second guide rollers 22u and 22d. In contrast, the bending wires 8l and 8r are extended to the upper side in FIG. 7 that is the other side inside the operation portion 3 through the guides 24, and guided to the second guide rollers 22l and 22r.

Thereafter, the respective bending wires 8u, 8d, 8l and 8r are extended in straight lines to the rotary bodies 9u, 9d, 9l and 9r from the second guide rollers 22u, 22d, 22l and 22r, and are extended in straight lines to the third guide rollers 23u, 23d, 23l and 23r from the rotary bodies 9u, 9d, 9l and 9r.

The respective bending wires 8u, 8d, 8l and 8r that are extended from the third guide rollers 23u, 23d, 23l and 23r are guided to the wire attachment portions 13u2, 13d2, 13l2 and 13r2 of the hanging frame 13 through the aforementioned first guide rollers 21u, 21d, 21l and 21r and fixed thereto.

According to this configuration, the respective bending wires 8u, 8d, 8l and 8r are smoothly pulled/slackened by a tilt operation of the operation element 5.

When the shaft portion 5a of the operation element 5 is in an upright state in a state in which the motor 12 is driven and the first pulley 11A1 and the second pulley 11A2 are rotated, the bending wires 8l and 8r that are respectively wound around the rotary bodies 9l and 9r disposed on the first pulley 11A1 enter a predetermined slackened state, and as a result the rotary bodies 9l and 9r enter a sliding state with respect to the first pulley 11A1.

In addition, by the bending wires 8u and 8d that are respectively wound around the rotary bodies 9u and 9d disposed on the second pulley 11A2 also entering a predetermined slackened state, the rotary bodies 9u and 9d enter a sliding state with respect to the second pulley 11A2.

As a result, the bending portion 2b is maintained in a straight state.

On the other hand, to cause the bending portion 2b to perform a bending operation, for example, in the upward direction, the operator tilts the operation element 5 in the arrow Yu direction in FIG. 1. Thereupon, accompanying the operation to tilt the operation element 5, the hanging frame 13 inclines, and the upward bending wire 8u fixed to the upward wire attachment portion 13u2 gradually changes from a slackened state to a tensed state. In contrast, the other bending wires 8d, 8l and 8r change to a state in which the bending wires are more slackened.

At this time, only the upward bending wire 8u that has been wound in a slackened state around the upward rotary body 9u of the second pulley 11A2 is pulled. Thereupon, the state between the upward rotary body 9u and the second pulley 11A2 changes to a closely contacting state. Further, frictional resistance arises between the upward rotary body 9u and the second pulley 11A2, and the upward rotary body 9u is rotated while sliding with respect to the second pulley 11A2 in the same direction as the second pulley 11A2. As a result, the upward bending wire 8u that is disposed further on the insertion portion 2 side than the upward rotary body 9u is pulled and moved accompanying rotation of the upward rotary body 9u, and the bending portion 2b starts a bending movement in the upward direction.

In this connection, when the operator continues the operation to tilt the operation element 5 so as to cause the upward rotary body 9u to closely contact the pulley 11, the bending portion 2b bends further in the upward direction as described above. Further, if the operator continues to maintain the tilt position of the operation element 5, the tensed state of the upward bending wire 8u and the slackened state of the bending wires 8d, 8l and 8r that are described above are maintained, and the bent state of the bending portion 2b is maintained. Subsequently, if the operator performs a tilt operation with respect to the operation element 5 to bend the bending portion 2b further in the same direction, to bend the bending portion 2b in another direction, or to return the bending portion 2b to the original state thereof, the bending portion 2b changes to a state that corresponds to the tilt operation of the operation element 5.

Thus, the configuration of the pulling member operation apparatus 10A includes the two pulleys 11A1 and 11A2 that are disposed in a perpendicular positional relationship with respect to the motor shaft 12b, and is provided with the driving force transmitting mechanism portion 30A that transmits a driving force of the motor 12 to the two pulleys 11A1 and 11A2.

According to this configuration, while preventing the diameter of the operation portion from becoming thick by making the length of the pulleys 11A1 and 11A2 shorter than the length of the pulley 11, similarly to the first embodiment, the bending portion 2b can be bent by a tilt operation of the operation element 5 which is erected vertically on the operation portion 3 that has a longitudinal axis parallel to the longitudinal axis of the insertion portion 2, and which intersects with the aforementioned longitudinal axis.

Further, the bending wire 8u that is led inside the operation portion 3 is guided to the first guide roller 21u by the second guide roller 22u, the rotary body 9u, and the third guide roller 23u that are disposed in a straight line, and is thereafter led to the wire attachment portion 13u2 of the hanging frame 13. The bending wire 8d is guided to the first guide roller 21d by the second guide roller 22d, the rotary body 9d, and the third guide roller 23d that are disposed in a straight line, and is thereafter led to the wire attachment portion 13d2 of the hanging frame 13. The bending wire 8l is guided to the first guide roller 21l by the second guide roller 22l, the rotary body 9l, and the third guide roller 23l that are disposed in a straight line, and is thereafter led to the wire attachment portion 13l2 of the hanging frame 13. Similarly, the bending wire 8r is guided to the first guide roller 21r by the second guide roller 22r, the rotary body 9r, and the third guide roller 23r that are disposed in a straight line, and is thereafter led to the wire attachment portion 13r2 of the hanging frame 13. Consequently, the bending wire travel paths can be simplified and a load applied to the respective bending wires 8u, 8d, 8l and 8r can be reduced.

Further, the rotary bodies 9l, 9r, 9u and 9d are disposed on the pulleys 11A1 and 11A2 so that the winding start positions 9s of the upward rotary body 9u and the downward rotary body 9d disposed on the second pulley 11A2 and the winding start positions 9s of the left rotary body 9l and the right rotary body 9r disposed on the first pulley 11A1 are separated by the maximum amount. Consequently, it is possible to reliably prevent the wires 8 from tangling together along the wire travel path.

In this connection, in the above described embodiment, a configuration is adopted in which the winding start positions 9s of the left rotary body 9l and the right rotary body 9r disposed on the first pulley 11A1 are set on the upper side in the drawings, and the winding start positions 9s of the upward rotary body 9u and the downward rotary body 9d disposed on the second pulley 11A2 are set on the lower side in the drawings.

However, as shown in a pulling member operation apparatus 10A1 illustrated in FIG. 8, a configuration may also be adopted in which the winding start positions 9s of the upward rotary body 9u and the downward rotary body 9d disposed on the second pulley 11A2 and the winding start positions 9s of the left rotary body 9l and the right rotary body 9r disposed on the first pulley 11A1 are disposed in the same direction.

In this case, a configuration is adopted in which a fourth gear (not shown) is added between the second spur gear 34 and the third spur gear 35 included in the driving force transmitting mechanism portion 30A, so that the first pulley 11A1 and the second pulley 11A2 are rotated in the same direction.

Further, according to the present embodiment, as shown in FIG. 9, an interval between the upward rotary body 9u and the downward rotary body 9d that are disposed on the second pulley 11A2 is set to a wider width than an interval between the left rotary body 9l and the right rotary body 9r that are disposed on the first pulley 11A1. The second guide rollers 22u, 22d, 22l and 22r and the third guide rollers 23u, 23d, 23l and 23r are disposed in a predetermined positional relationship with respect to the rotary bodies 9u, 9d, 9l and 9r.

In this connection, when the thickness of the respective rotary bodies 9 is taken as t, a relation w7<2t is set between an interval w7 between the left rotary body 9l and the right rotary body 9r and the thickness t. Thus, entanglement between the wires 8 along the wire travel path is prevented.

Note that, although not illustrated in the drawings, for example, a configuration may also be adopted in which the diametrical dimensions of the upward rotary body 9u and the downward rotary body 9d are larger than the diametrical dimensions of the left rotary body 9l and the right rotary body 9r.

According to this configuration, entanglement between the wires 8 along the wire travel path can be prevented and the amount of pulling force can be increased when pulling the upward bending wire 8u and the downward bending wire 8d. Consequently, a bending operation in the vertical direction for which the bending angle is large in comparison to a bending operation in the lateral direction can be performed more smoothly.

A second embodiment of the present invention will now be described referring to FIG. 10 to FIG. 15.

Figure 10:
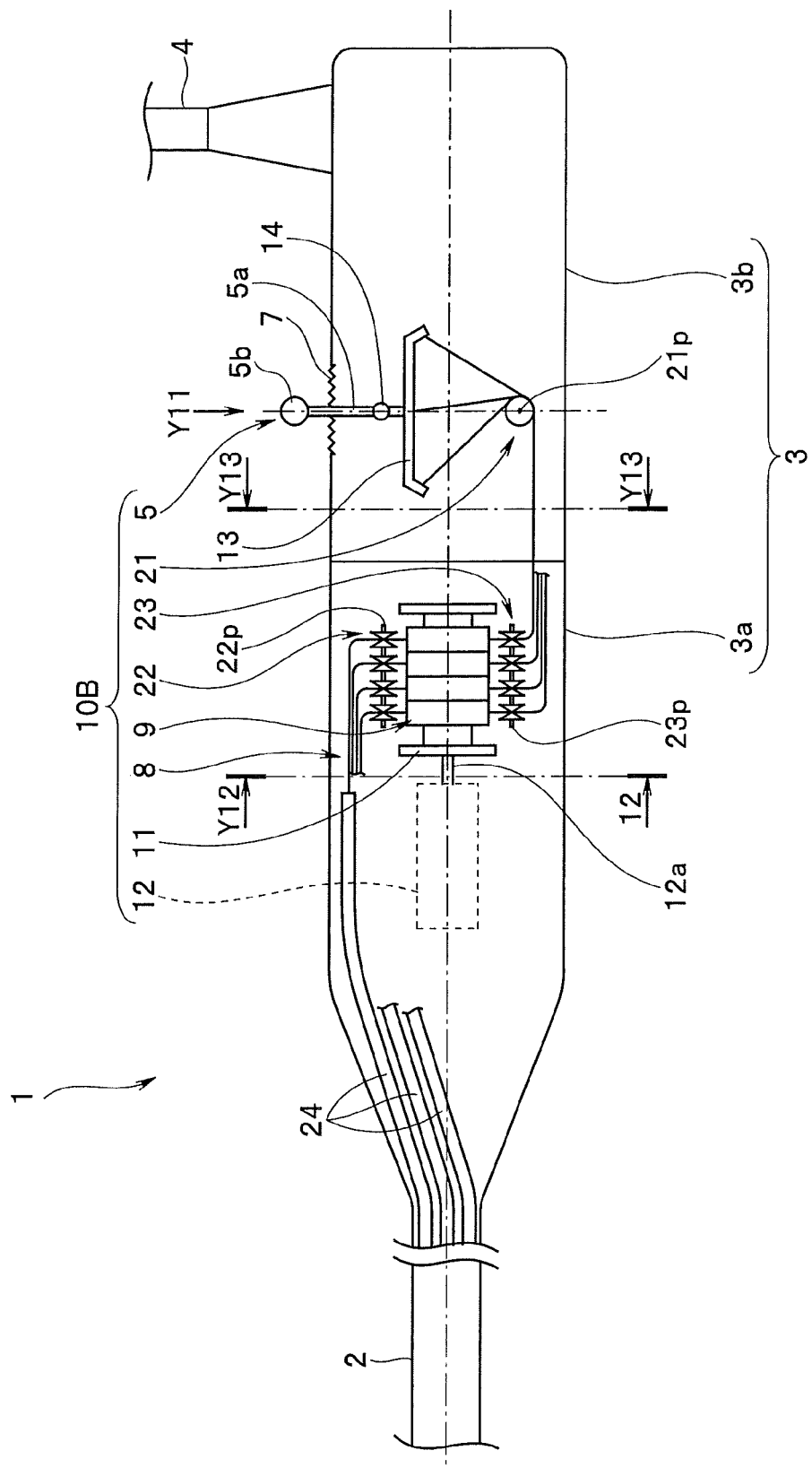
Figure 11:
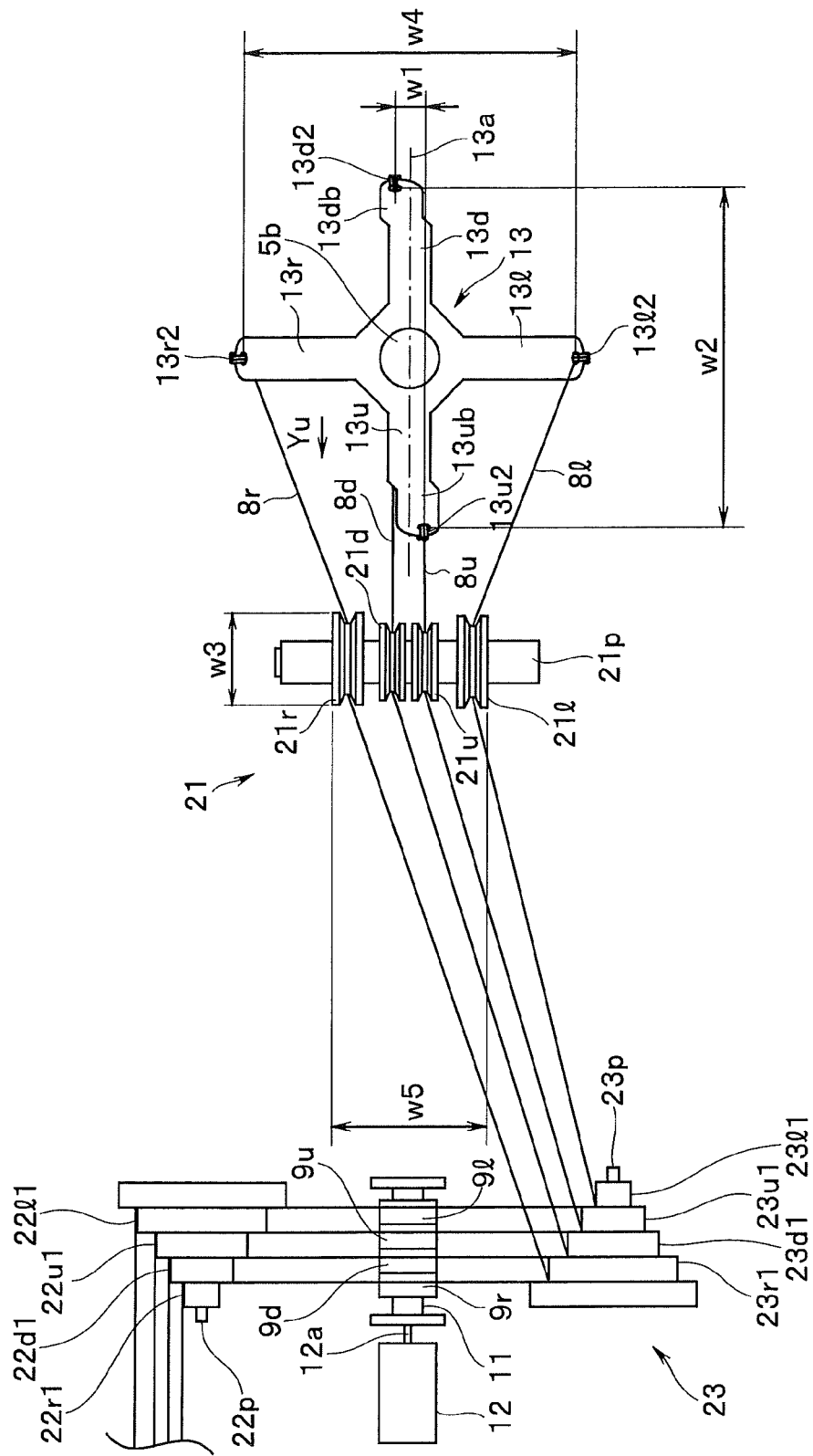
Figure 12:
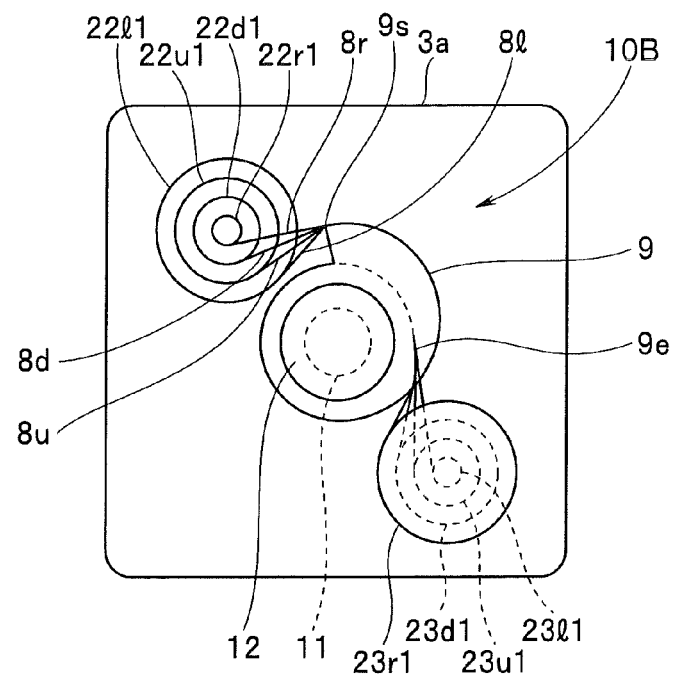
Figure 13:
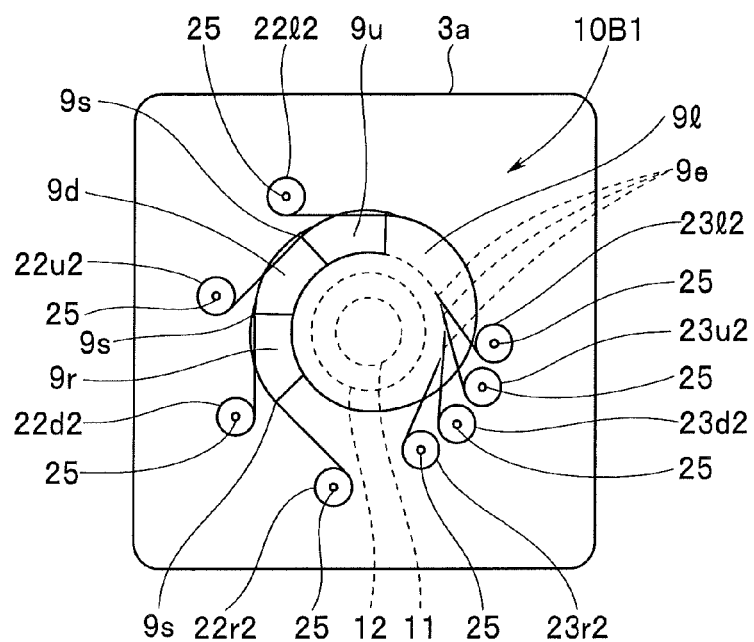
Figure 14:
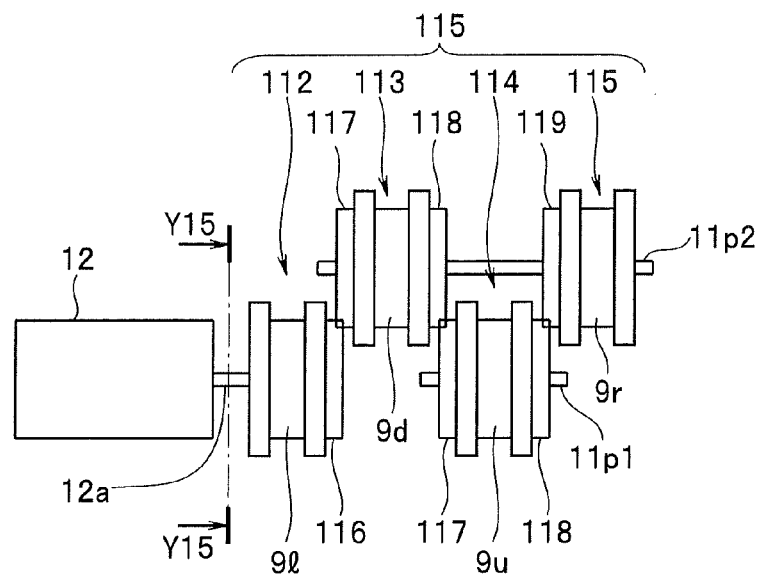
Figure 15:
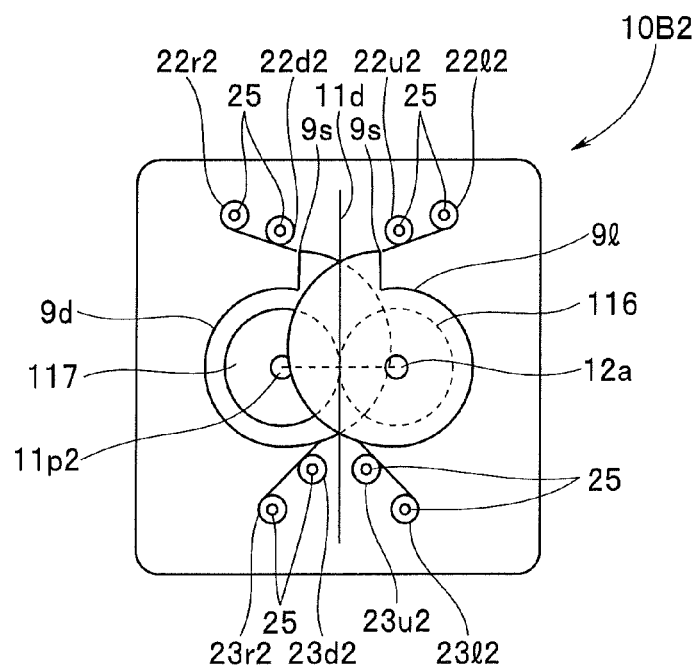

FIG. 10 is a view that illustrates another configuration of a pulling member operation apparatus that contains a motor and a pulley in an operation portion that includes a grasping portion and an operation portion body. FIG. 11 is a view that illustrates the pulling member operation apparatus as viewed from the arrow Y11 direction in FIG. 10. FIG. 12 is a view that illustrates a configuration example of a second guide roller, a third guide roller, and a plurality of rotary bodies disposed on a pulley as viewed from the direction of a line indicated by arrows Y12-Y12 in FIG. 10. FIG. 13 is a view that illustrates a configuration example of a plurality of second guide rollers, a plurality of third guide rollers, and a plurality of rotary bodies disposed on a pulley as viewed from the direction of a line indicated by arrows Y13-Y13 in FIG. 10, that is a modification example of the arrangement positions of guide rollers. FIG. 14 is a view that illustrates a pulley having a configuration that includes a plurality of shaft bodies, that is a modification example of a pulley. FIG. 15 is a view that illustrates the pulley as viewed from the direction of a line indicated by arrows Y15-Y15 in FIG. 14.

As shown in FIG. 10, a pulling member operation apparatus 10B that is provided inside an operation portion 3 is mainly constituted by four bending wires 8, an elongated pulley 11 on which four rotary bodies 9 are arranged, a motor 12, a hanging frame 13, an operation element 5, and a plurality of guide roller sets 21, 22 and 23 that include a plurality of guide rollers that are wire travel path changing members.

In the present embodiment also, a configuration is adopted so that the center of gravity of the operation portion 3 is positioned inside the grasping portion 3a.

In the present embodiment, the pulley 11 and the motor 12 are disposed at predetermined positions inside the grasping portion 3a so that the longitudinal axis of the pulley 11 and the drive shaft of the motor 12 are in a parallel positional relationship with respect to the longitudinal axis of the grasping portion 3a, respectively. According to this configuration, the pulley 11 is integrally fixed to a shaft portion 12a of the motor 12, and is configured to be directly rotated around its axis by the driving force of the motor 12.

In this connection, a configuration may also be adopted in which the longitudinal axis of the pulley 11 and the drive shaft of the motor 12 are coaxial with respect to the longitudinal axis of the grasping portion 3a.

As shown in FIG. 10 and FIG. 11, the first guide roller set 21 is an attachment path setting member that includes the first guide rollers 21u, 21d, 21l and 21r that are the aforementioned first wire travel path changing member. The second guide roller set 22 is a pulley lead-in member that includes the second guide rollers 22u1, 22d1, 22l1 and 22r1 that are second wire travel path changing members. The third guide roller set 23 is a pulley lead-out member that includes the third guide rollers 23u1, 23d1, 23l1 and 23r1 that are third wire travel path changing members.

In the present embodiment, the second guide roller set 22 includes, for example, a cylindrical second roller shaft 22p that is a support body, and second guide rollers 22u1, 22d1, 22l1 and 22r1 that change wire travel paths. The second guide rollers 22u1, 22d1, 22l1 and 22r1 are pivotably disposed on the second roller shaft 22p.

The third guide roller set 23 includes a third roller shaft 23p, and third guide rollers 23u1, 23d1, 23l1 and 23r1 that change wire travel paths. The third guide rollers 23u1, 23d1, 23l1 and 23r1 are pivotably disposed on the third roller shaft 23p.

The second roller shaft 22p and the third roller shaft 23p are disposed at predetermined positions in a parallel positional relationship with respect to the longitudinal axis of the grasping portion 3a.

In this connection, the first roller shaft 21p, the second roller shaft 22p, and the third roller shaft 23p may be different members or may be the same member.

In the present embodiment, with respect to the respective bending wires 8u, 8d, 8l and 8r that pass through the inside of the insertion portion 2 and are led into the operation portion 3, first, the travel paths thereof are changed by the second guide rollers 22u1, 22d1, 22l1 and 22r1 of the second guide roller set 22, and thereafter the respective bending wires 8u, 8d, 8l and 8r pass through the winding start positions 9s of the rotary bodies 9u, 9d, 9l and 9r and are wound around the rotary bodies 9u, 9d, 9l and 9r, respectively.

Next, after being wound around the rotary bodies 9u, 9d, 9l and 9r, the travel paths of the respective bending wires 8u, 8d, 8l and 8r that are led out from the winding end positions 9e are changed by the third guide rollers 23u1, 23d1, 23l1 and 23r1 of the third guide roller set 23 so that the respective bending wires 8u, 8d, 8l and 8r travel in the direction of the first guide rollers 21u, 21d, 21l and 21r of the first guide roller set 21.

Further, the travel paths of the respective bending wires 8u, 8d, 8l and 8r are changed by the first guide rollers 21u, 21d, 21l and 21r as described above so that the bending wires 8u, 8d, 8l and 8r arrive at the upward wire attachment portion 13u2, the downward wire attachment portion 13d2, the left wire attachment portion 13l2, and the right wire attachment portion 13r2 of the hanging frame 13.

In this connection, in FIG. 11 also, in order to describe the positional relation between the respective bending wires 8u, 8d, 8l and 8r and the respective wire attachment portions 13u2, 13d2, 13l2 and 13r2, the position of the hanging frame 13 is displaced in the right direction in the drawing with respect to the roller shaft 21p.

In the present embodiment, the first guide rollers 21u, 21d, 21l and 21r are configured in the same manner as in the above described embodiment and are disposed on the first roller shaft 21p.

In contrast, with regard to the second guide rollers 22u1, 22d1, 22l1 and 22r1, the diametrical dimensions thereof are set so that the diametrical dimensions of the second guide rollers 22u1, 22d1, 22l1 and 22r1 increase in the order of second guide roller 22r1, second guide roller 22d1, second guide roller 22u1 and second guide roller 22l1. Further, the second roller shaft 22p is disposed so that the diametrical dimension thereof increases from the insertion portion 2 side toward the operation element 5 side.

The diametrical dimensions of the third guide rollers 23u1, 23d1, 23l1 and 23r1 are also different to each other. In the third guide rollers 23u1, 23d1, 23l1 and 23r1, in the opposite manner to the second guide rollers 22r1, 22d1, 22u1 and 22l1, the diametrical dimensions are set so that the diametrical dimensions decrease in the order of third guide roller 23r1, third guide roller 23d1, third guide roller 23u1 and third guide roller 23l1. Further, the third roller shaft 23p is disposed so that the diametrical dimension thereof decreases from the insertion portion 2 side toward the operation element 5 side.

The rotary bodies 9r, 9d, 9u and 9l are disposed on the pulley 11 from the insertion portion 2 side towards the operation element 5 side. As shown in FIG. 10 and FIG. 11, the second guide rollers 22r1, 22d1, 22u1 and 22l1 of the second guide roller set 22 and the guide rollers 23r1, 23d1, 23u1 and 23l1 of the third guide roller set 23 are disposed at predetermined positions in a positional relationship in which the second guide rollers 22r1, 22d1, 22u1 and 22l1 and the guide rollers 23r1, 23d1, 23u1 and 23l1 face each other in a manner such that the rotary bodies 9r, 9d, 9u and 9l of the pulley 11 are interposed therebetween.

The travel paths inside the operation portion 3 of the respective bending wires 8u, 8d, 8l and 8r will now be described referring to FIG. 10, FIG. 11 and FIG. 12.

As shown in FIG. 11, the respective proximal end portions of the four bending wires 8u, 8d, 8l and 8r are fixed to the wire attachment portions 13u2, 13d2, 13l2 and 13r2.

In contrast, as described above, the distal end portions of the respective bending wires 8u, 8d, 8l and 8r are fixed at positions corresponding to upward, downward, left and right of the distal end bending pieces.

As shown in FIG. 10, the bending wires 8u, 8d, 8l and 8r that are fixed to the distal end bending pieces are extended inside the operation portion 3 through the guides 24. As shown in FIG. 10, FIG. 11 and FIG. 12, the respective bending wires 8u, 8d, 8l and 8r are guided to the second guide rollers 22u1, 22d1, 22l1 and 22r1, and the wire travel paths are changed.

As described above, the diametrical dimensions of the second guide rollers 22u1, 22d1, 22l1 and 22r1 are different to each other, and the second guide rollers 22u1, 22d1, 22l1 and 22r1 are disposed on the second roller shaft 22p so that the diametrical dimensions increase from the insertion portion 2 side towards the operation element 5 side. Consequently, the respective bending wires 8u, 8d, 8l and 8r enter onto the second guide rollers 22u1, 22d1, 22l1 and 22r1 and thereafter exit therefrom without the wires interfering with each other. As a result, the travel paths are changed without the bending wires 8u, 8d, 8l and 8r tangling together.

The bending wires 8u, 8d, 8l and 8r whose travel paths have been changed at the second guide rollers 22u1, 22d1, 22l1 and 22r1 are wound around the rotary bodies 9u, 9d, 9l and 9r that are disposed in a loosely fitting state on the pulley 11. More specifically, the respective bending wires 8u, 8d, 8l and 8r are wound around the rotary bodies 9u, 9d, 9l and 9r, respectively, so as to be in a predetermined slackened state from the respective winding start positions 9s. Further, the respective bending wires 8u, 8d, 8l and 8r are led out towards the third guide rollers 23u1, 23d1, 23l1 and 23r1 from the winding end positions 9e of the rotary bodies 9u, 9d, 9l and 9r.

As described above, the second guide rollers 22r1, 22d1, 22u1 and 22l1 and the third guide rollers 23r1, 23d1, 23u1 and 23l1 are disposed in a facing positional relationship in a manner that interposes the rotary bodies 9r, 9d, 9u and 9l therebetween. Accordingly, the bending wires 8u, 8d, 8l and 8r are led out from the rotary bodies 9u, 9d, 9l and 9r without the wires tangling together.

The respective bending wires 8u, 8d, 8l and 8r that are led out from the rotary bodies 9u, 9d, 9l and 9r are led into the third guide rollers 23u1, 23d1, 23l1 and 23r1, and thereafter the wire travel paths thereof are changed in the direction of the first guide rollers 21u1, 21d1, 21l1, and 21r1.

As described above, the diametrical dimensions of the third guide rollers 23u1, 23d1, 23l1 and 23r1 are different, and the third guide rollers 23u1, 23d1, 23l1 and 23r1 are disposed on the third roller shaft 23p so that the diametrical dimensions decrease from the insertion portion 2 side to the operation element 5 side. Consequently, the respective bending wires 8u, 8d, 8l and 8r enter onto the third guide rollers 23u1, 23d1, 23l1 and 23r1 and thereafter exit therefrom without the wires interfering with each other. As a result, the travel paths are changed without the bending wires 8u, 8d, 8l and 8r tangling together.

The first wires 8u, 8d, 8l and 8r whose travel paths have been changed at the first guide rollers 21u, 21d, 21l and 21r are guided to and fixed to the wire attachment portions 13u2, 13d2, 13l2 and 13r2 included in the hanging frame 13 as described above.

The remaining configuration is the same as in the above described embodiment, and the same members are denoted by the same reference symbols, and a description of such members is omitted.

Thus, in the configuration in which the pulley 11 and the motor 12 are disposed inside the operation portion 3 that has a longitudinal axis that is parallel to the longitudinal axis of the insertion portion 2 included in the endoscope 1, the longitudinal axis of the pulley 11 and the drive shaft of the motor 12 are disposed parallel to the longitudinal axis of the grasping portion 3a.

In addition, the guide roller sets 22 and 23 having the roller shafts 22p and 23p that are parallel to the longitudinal axis of the operation portion 3, and the first guide roller set 21 having the first roller shaft 21p that intersects at right angles with the longitudinal axis of the operation portion 3 are disposed at predetermined positions as wire travel path changing members.

Further, the travel paths of the respective bending wires 8u, 8d, 8l and 8r that are led into the operation portion 3 and travel towards the proximal end side of the operation portion 3 are changed in the direction of the winding start positions 9s of the rotary bodies 9u, 9d, 9l and 9r that are disposed on the pulley 11 by the second guide rollers 22u1, 22d1, 22l1 and 22r1.

Furthermore, the travel paths of the respective bending wires 8u, 8d, 8l and 8r that are led out from the winding end positions of the rotary bodies 9u, 9d, 9l and 9r are changed in the direction of the first guide rollers 21u, 21d, 21l and 21r by the third guide rollers 23u1, 23d1, 23l1 and 23r1.

Finally, the travel paths of the respective bending wires 8u, 8d, 8l and 8r are changed by the first guide rollers 21u, 21d, 21l and 21r, and the respective bending wires 8u, 8d, 8l and 8r are led to the wire attachment portions 13u2, 13d2, 13l2 and 13r2 of the hanging frame 13 are fixed thereto.

According to the endoscope 1 configured in the above described manner, in a state in which the motor 12 is driven and the pulley 11 is rotated, when the shaft portion 5a of the operation element 5 is in an upright state, similarly to the above described embodiment, each of the bending wires 8u, 8d, 8l and 8r that are wound around the rotary bodies 9u, 9d, 9l and 9r disposed on the pulley 11, respectively, enters a predetermined slackened state, and the bending portion 2b is maintained in a straight state.

On the other hand, in a state in which the operator has grasped the grasping portion 3a, to cause the bending portion 2b to perform a bending operation in, for example, the upward direction, the operator places the ball of the thumb on the finger contact portion 5b of the operation element 5 and tilts the shaft portion 5a in the direction of the arrow Yu in FIG. 1. Thereupon, similarly to the above described embodiment, accompanying the operation to tilt the operation element 5, the hanging frame 13 inclines, and the upward bending wire 8u that is fixed to the upward wire attachment portion 13u2 gradually changes from a slackened state to a tensed state. As a result, among the respective bending wires 8u, 8d, 8l and 8r that have been wound in a slackened state around the rotary bodies 9u, 9d, 9l and 9r of the pulley 11, only the upward bending wire 8u is pulled. Thereupon, the gap 9c of the upward rotary body 9u is narrowed in resistance to the elastic force and is contracted, and the state changes to one in which the upward rotary body 9u and the pulley 11 are in a closely contacting state. As a result, frictional resistance arises between the upward rotary body 9u and the pulley 11, and the upward rotary body 9u is rotated while sliding with respect to the pulley 11 in the same direction as the pulley 11. Consequently, the upward bending wire 8u that is disposed further on the insertion portion 2 side than the upward rotary body 9u is pulled and moved accompanying rotation of the upward rotary body 9u, and the bending portion 2b starts a bending movement in the upward direction.

Thereafter, if the operator continues the operation to tilt the shaft portion 5a in the same direction so as to cause the upward rotary body 9u to closely contact the pulley 11, the upward rotary body 9u that is in the closely contacting state is brought into even closer contact with the pulley 11 and the frictional force increases further. As a result, the wire for upward bending 8u that is disposed at a position that is further on the insertion portion 2 side than the upward rotary body 9u is pulled and moved to a further degree accompanying rotation of the rotary body 9u, and thus the bending portion 2b bends further in the upward direction.

In contrast, if the operator continues to maintain the tilt position of the operation element 5, the tightness between the upward rotary body 9u and the pulley 11 is maintained. Thus, movement stops in a state in which a tensile force has arisen at the upward bending wire 8u disposed at a position that is further on the distal end side than the upward rotary body 9u.

At this time, each of the bending wires 8d, 8l and 8r is in a slackened state. Accordingly, by continuing to maintain the operation element 5 in this tilted state, the tensed state of the upward bending wire 8u and the slackened state of the bending wires 8d, 8l and 8r are maintained, respectively, and the bending portion 2b is maintained in the bent state.

According to this configuration, by disposing the motor 12 and the pulley 11 on the same axis, the same actions and effects as described above are obtained while directly driving the pulley 11 by the driving force of the motor 12.

In this connection, in the above described embodiment a configuration is adopted in which the second guide roller set 22 that includes the second guide rollers 22u1, 22d1, 22l1 and 22r1 and the third guide roller set 23 that includes the third guide rollers 23u1, 23d1, 23l1 and 23r1 are disposed in a facing positional relationship in a manner that interposes the rotary bodies 9u, 9d, 9l and 9r disposed on the pulley 11 therebetween. However, a configuration may also be adopted in which, as shown in FIG. 13, the second guide rollers 22r, 22d, 22u and 22l and the third guide rollers 23r, 23d, 23u and 23l are not configured as a guide roller set, but are individually disposed at predetermined positions.

As shown in FIG. 13, the diametrical dimensions of the second guide rollers 22r2, 22d2, 22u2 and 22l2 of the present embodiment and the third guide rollers 23r2, 23d2, 22u2 and 23l2 are the same. In addition, each of the second guide rollers 22r2, 22d2, 22u2 and 22l2 and each of the third guide rollers 23r2, 23d2, 23u2 and 23l2 are pivotably provided in an individual manner on a roller shaft 25. Further, each of the second guide rollers 22r2, 22d2, 22u2 and 22l2 and each of the third guide rollers 23r2, 23d2, 23u2 and 23l2 are individually disposed at a predetermined position by deviating the positions thereof in the circumferential direction with respect to the outer circumference of the pulley 11 on which the rotary bodies 9r, 9d, 9u and 9l are disposed. The remaining configuration of the pulling member operation apparatus 10B1 is the same as in the above described embodiment.

According to the above described configuration, the respective bending wires 8u, 8d, 8l and 8r that are extended into the operation portion 3 through the guides 24 are guided to the corresponding second guide rollers 22u2, 22d2, 22l2 and 22r2 and the wire travel paths are changed. The second guide rollers 22u2, 22d2, 22l2 and 22r2 are pivotably disposed at predetermined positions with respect to the rotary bodies 9u, 9d, 9l and 9r. Consequently, the respective bending wires 8u, 8d, 8l and 8r enter onto the second guide rollers 22u2, 22d2, 22l2 and 22r2 and thereafter exit therefrom without the wires interfering with each other. As a result, the travel paths are changed without the bending wires 8u, 8d, 8l and 8r tangling together.

Further, the respective bending wires 8u, 8d, 8l and 8r that are led out from the rotary bodies 9u, 9d, 9l and 9r are led into the third guide rollers 23u2, 23d2, 23l2 and 23r2, and thereafter the wire travel paths are changed in the direction of the first guide rollers 21u, 21d, 21l, and 21r.

The third guide rollers 23u2, 23d2, 23l2 and 23r2 are pivotably disposed at predetermined positions with respect to the rotary bodies 9u, 9d, 9l and 9r. Consequently, the respective bending wires 8u, 8d, 8l and 8r enter onto the third guide rollers 23u2, 23d2, 23l2 and 23r2 and thereafter exit therefrom without the wires interfering with each other. As a result, the travel paths are changed without the bending wires 8u, 8d, 8l and 8r tangling together.

Thus, the same actions and effects as in the above described embodiment can be obtained.

Further, in the above described second embodiment, a configuration is adopted in which the four rotary bodies 9u, 9d, 9l and 9r are disposed on the elongated pulley 11. However, the configuration of the pulley 11 and the rotary bodies 9u, 9d, 9l and 9r are not limited thereto, and a configuration of a pulley 111 as shown in FIG. 14 and FIG. 15 may be adopted.

The pulley 111 in a pulling member operation apparatus 10B2 of the present embodiment that is shown in FIG. 14 and FIG. 15 includes a first shaft body 112 that is fixed to the shaft portion 12a of the motor 12 on which the rotary body 9 is disposed in a predetermined loosely fitting state, two second shaft bodies 113 and 114 on which the rotary bodies 9 are disposed in a predetermined loosely fitting state, respectively, and a third shaft body 115 on which the rotary body 9 is disposed in a predetermined loosely fitting state.

The first shaft body 112 includes a fixing section (unshown) on which the shaft portion 12a of the motor 12 is arranged on one surface side, and has a geared protrusion 116 on the other surface side. The second shaft bodies 113 and 114 each have a geared protrusion 117 on one surface side and have a geared protrusion 118 on the other surface side. The third shaft body 115 has a geared protrusion 119 on one surface side.

The geared protrusion 117 of the second shaft body 113 intermeshes with the geared protrusion 116 of the first shaft body 112. The geared protrusion 117 of the second shaft body 114 intermeshes with the geared protrusion 118 of the second shaft body 113. Further, the geared protrusion 119 of the third shaft body 115 intermeshes with the geared protrusion 118 of the second shaft body 114.

According to this configuration, when the motor 12 enters a driving state, the first shaft body 112 included in the pulley 111 is rotated by the driving force of the motor 12. Further, the second shaft body 113, the second shaft body 114 and the third shaft body 115 included in the pulley 111 are respectively rotated as the result of the rotation of the first shaft body 112 being transmitted thereto via the geared protrusions 116, 117, 118 and 119.

As a result, according to the present embodiment, the first shaft body 112 and the second shaft body 114, for example, rotate counterclockwise, and the second shaft body 113 and the third shaft body 115, for example, rotate clockwise.

In this connection, according to the present embodiment, the rotary body 9 disposed on the first shaft body 112 acts as the left rotary body 9l, the rotary body 9 disposed on the second shaft body 113 acts as the downward rotary body 9d, the rotary body 9 disposed on the second shaft body 114 acts as the upward rotary body 9u, and the rotary body 9 disposed on the third shaft body 115 acts as the right rotary body 9r.

Further, reference symbol 11p1 denotes a first pulley shaft that pivotably supports the second shaft body 114. The shaft center of the first pulley shaft 11p1 and the shaft center of the motor shaft 12b coincide. Reference symbol 11p2 denotes a second pulley shaft that pivotably supports the second shaft body 113 and the third shaft body 115.

As shown in FIG. 15, the axis of the left rotary body 9l and the axis of the upward rotary body 9u deviate with respect to the axis of the downward rotary body 9d and the axis of the right rotary body 9r. Further, the left rotary body 9l and the upward rotary body 9u are disposed in an opposite direction to the downward rotary body 9d and the right rotary body 9r.

As a result, the second guide rollers 22r2 and 22d2 and the second guide rollers 22u2 and 22l2 are disposed at predetermined positions with respect to the rotary bodies 9u, 9d, 9l and 9r in a facing positional relationship in a manner that interposes a dividing line 11d therebetween. The dividing line 11d is orthogonal to the center of a line segment that joins the shaft center of the motor shaft 12a and the shaft center of the second pulley shaft 11p2.

Further, the third guide rollers 23r2 and 23d2 and the third guide rollers 23u2 and 23l2 are also disposed at predetermined positions with respect to the rotary bodies 9u, 9d, 9l and 9r in a facing positional relationship in a manner that interposes the dividing line 11d therebetween. The remaining configuration is the same as in the above described embodiment. According to the above configuration, the respective bending wires 8u, 8d, 8l and 8r that extend inside the operation portion 3 through the guides 24 are guided to the second guide rollers 22u2, 22d2, 22l2 and 22r2 that are provided in pairs on either side of the dividing line 11d, and the wire travel paths are changed. Further, the respective bending wires 8u, 8d, 8l and 8r that are led out from the rotary bodies 9u, 9d, 9l and 9r are also guided on the third guide rollers 23u2, 23d2, 23l2 and 23r2 that are provided in pairs on either side of the dividing line 11d, and thereafter the wire travel paths are changed in the direction of the first guide rollers 21u, 21d, 21l and 21r.

Thus, the travel paths of the bending wires 8 are changed by the second guide rollers 22u2 and 22l2 and the second guide rollers 22d2 and 22r2, as well as the third guide rollers 23u2 and 23l2 and the third guide rollers 23d2 and 23r2 that are provided in pairs on either side of the dividing line 11d. Consequently, interference between the bending wires 8u, 8d, 8l and 8r can be reliably prevented, and the travel paths can be changed without the bending wires 8u, 8d, 8l and 8r tangling together.

Thus, the same actions and effects as the above described embodiment can be obtained.

Figure 16:
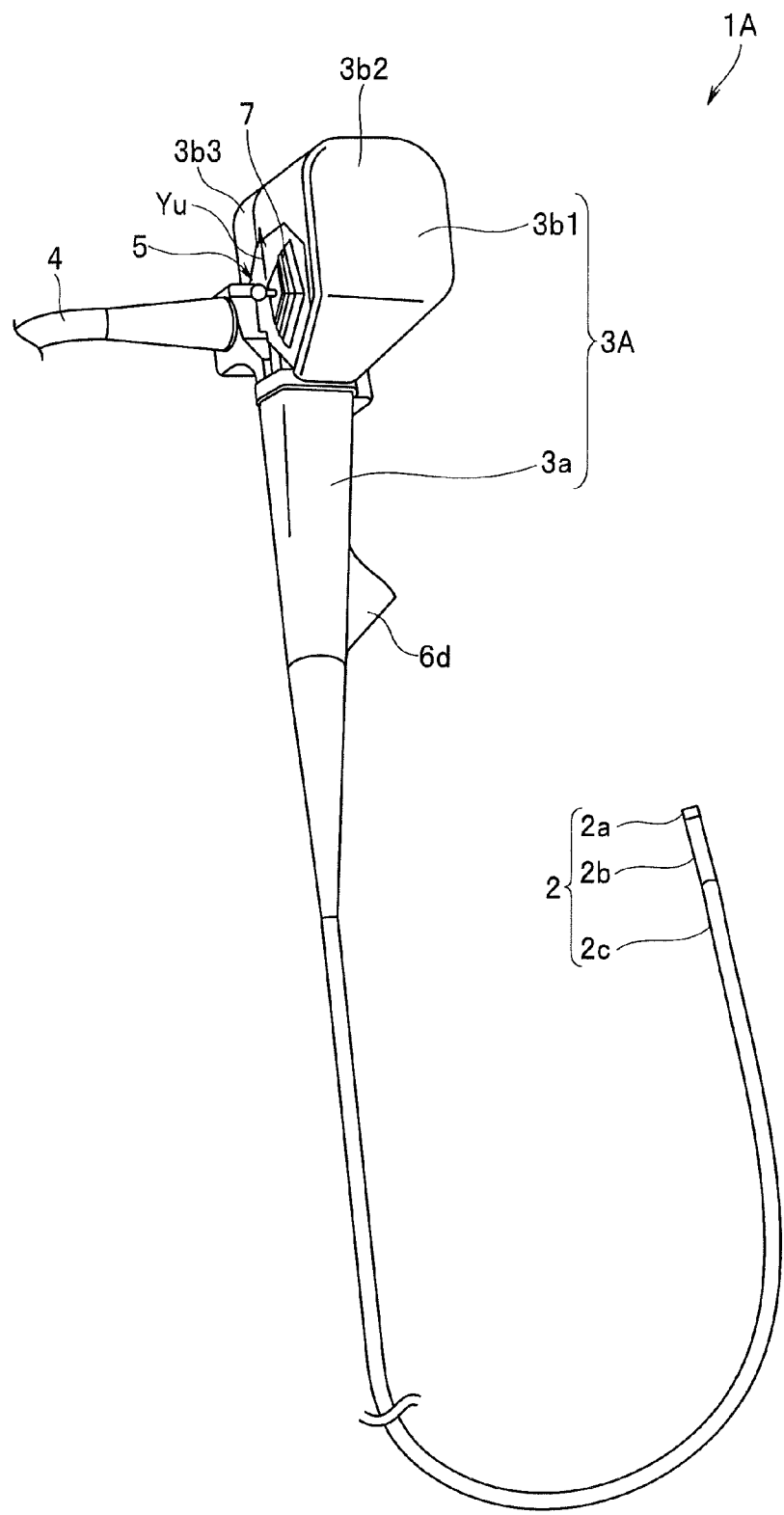
Figure 17:
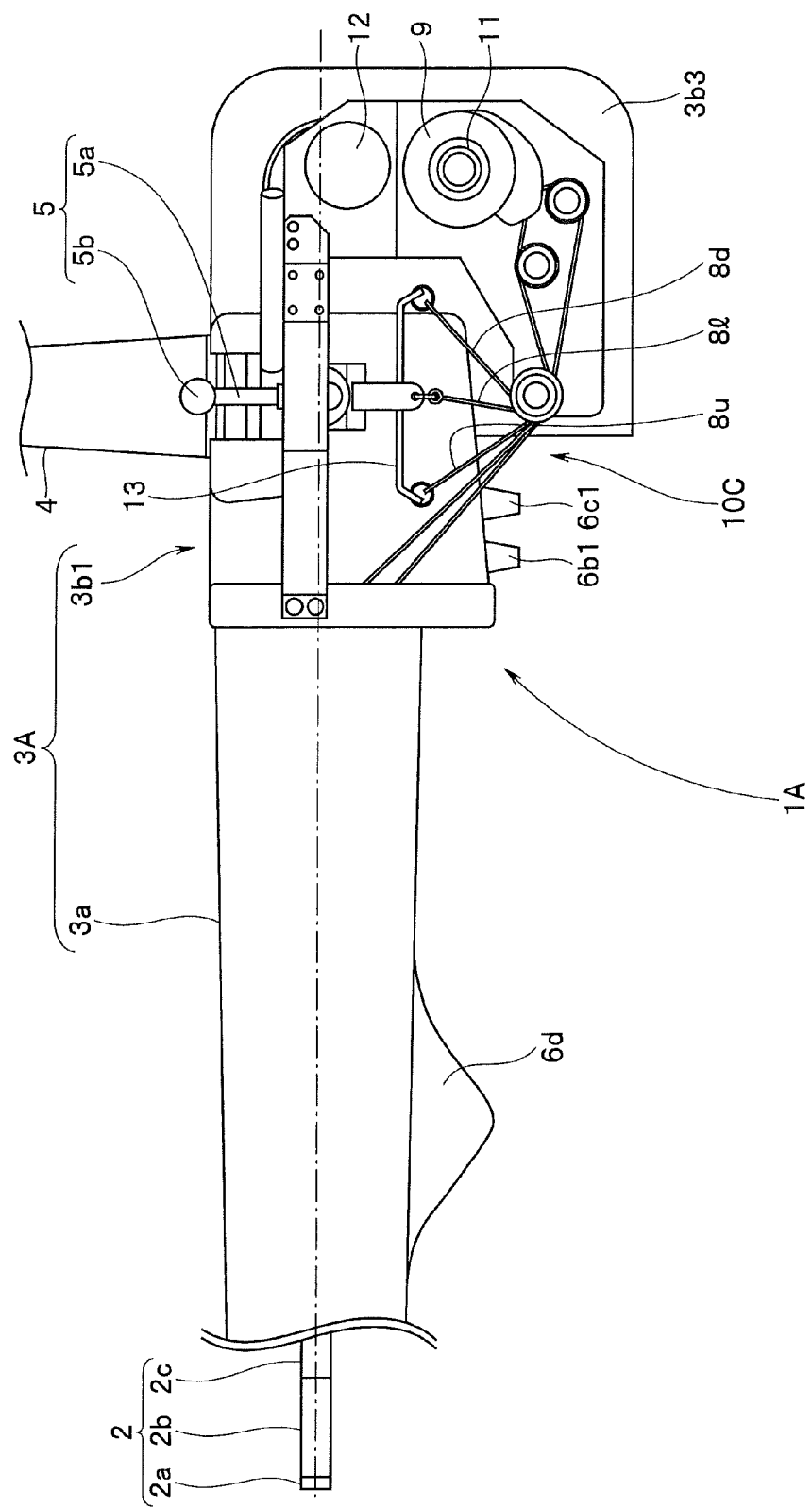
Figure 18:
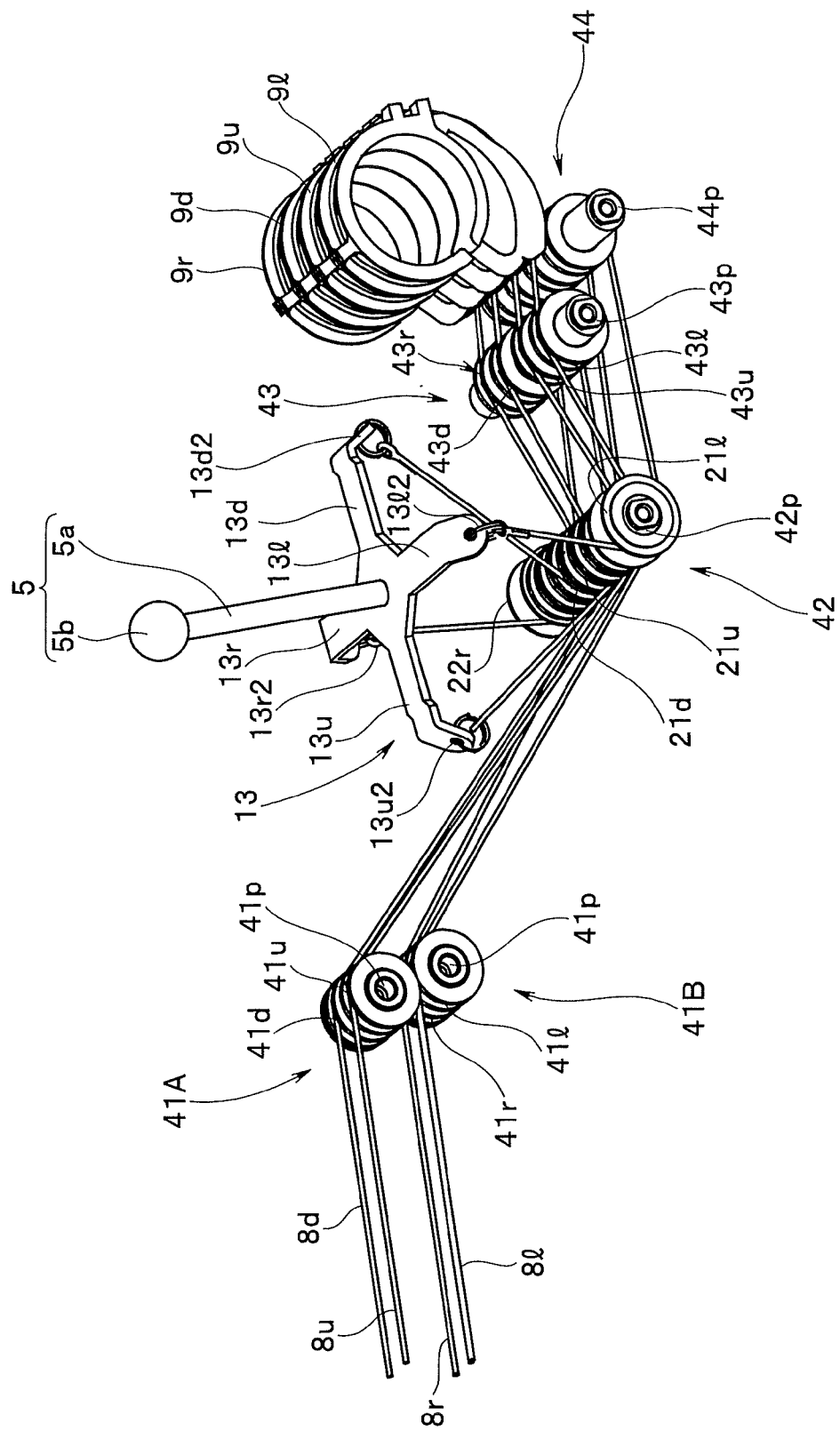
Figure 19:
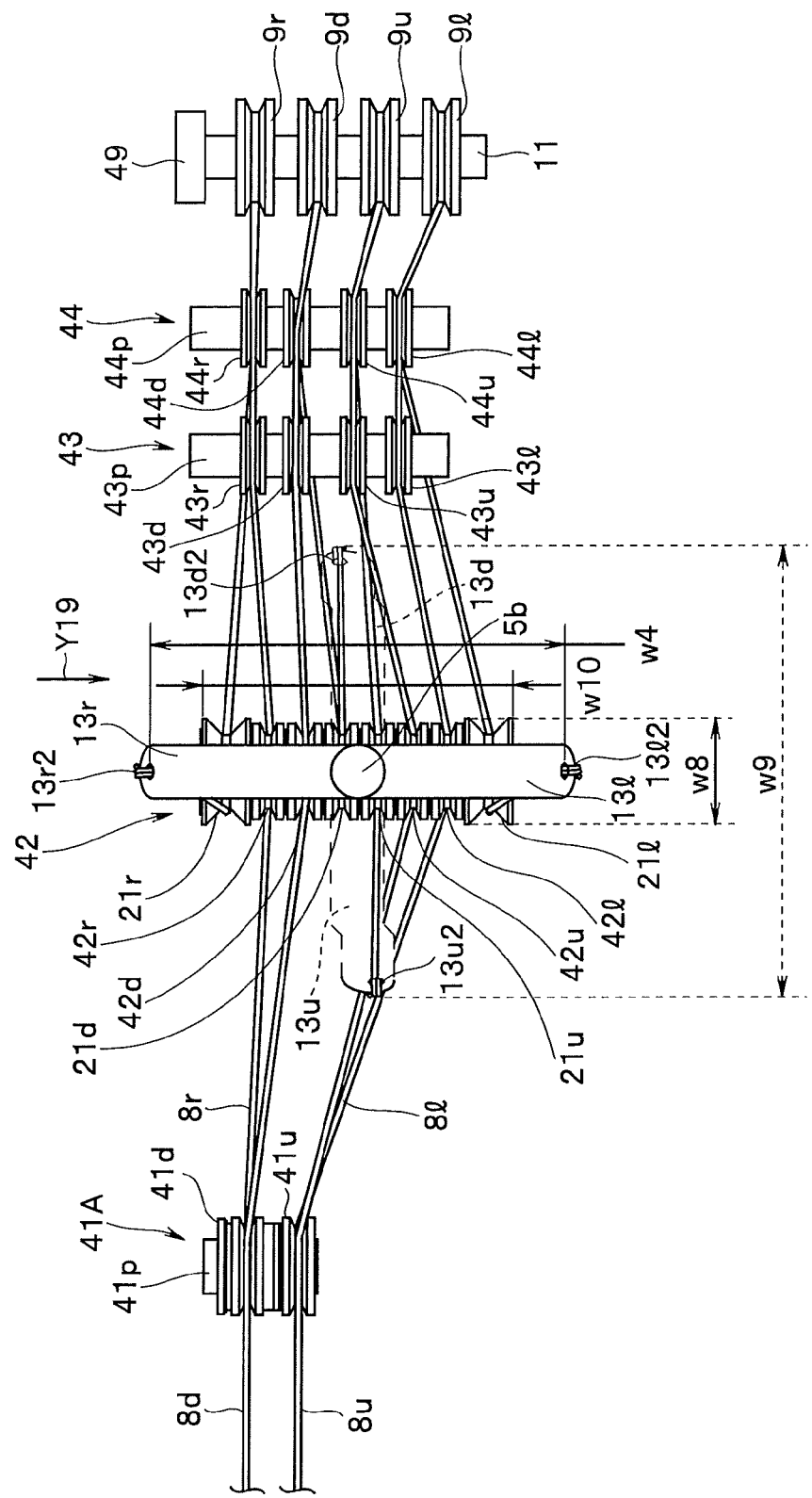
Figure 20:
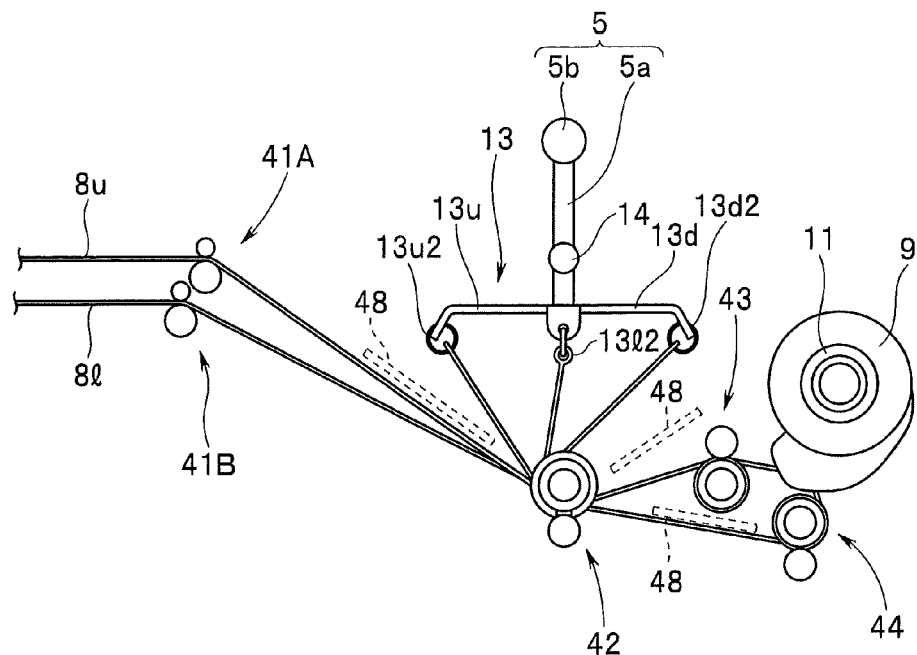
Figure 22:
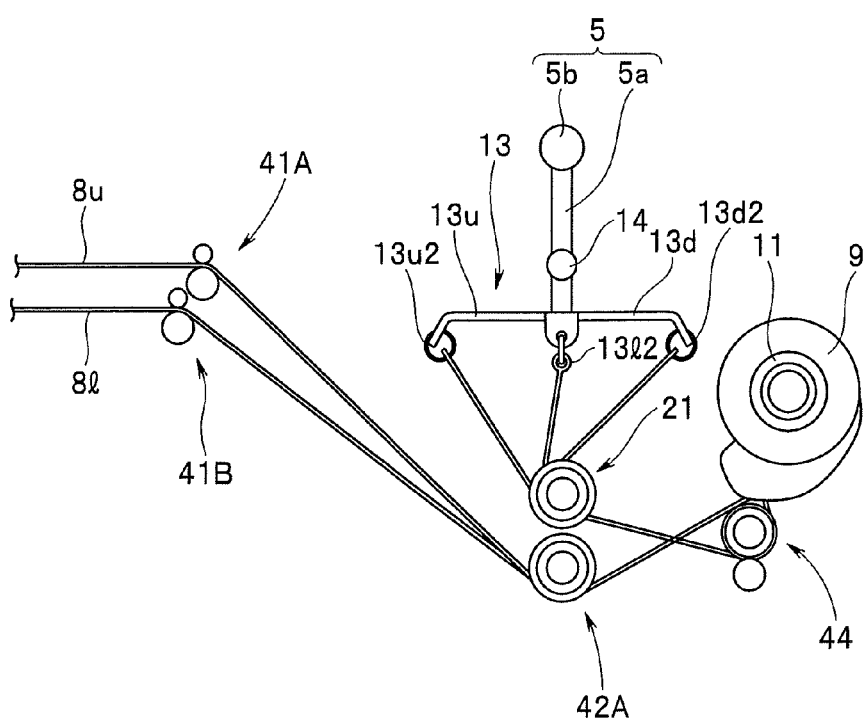
Figure 21:
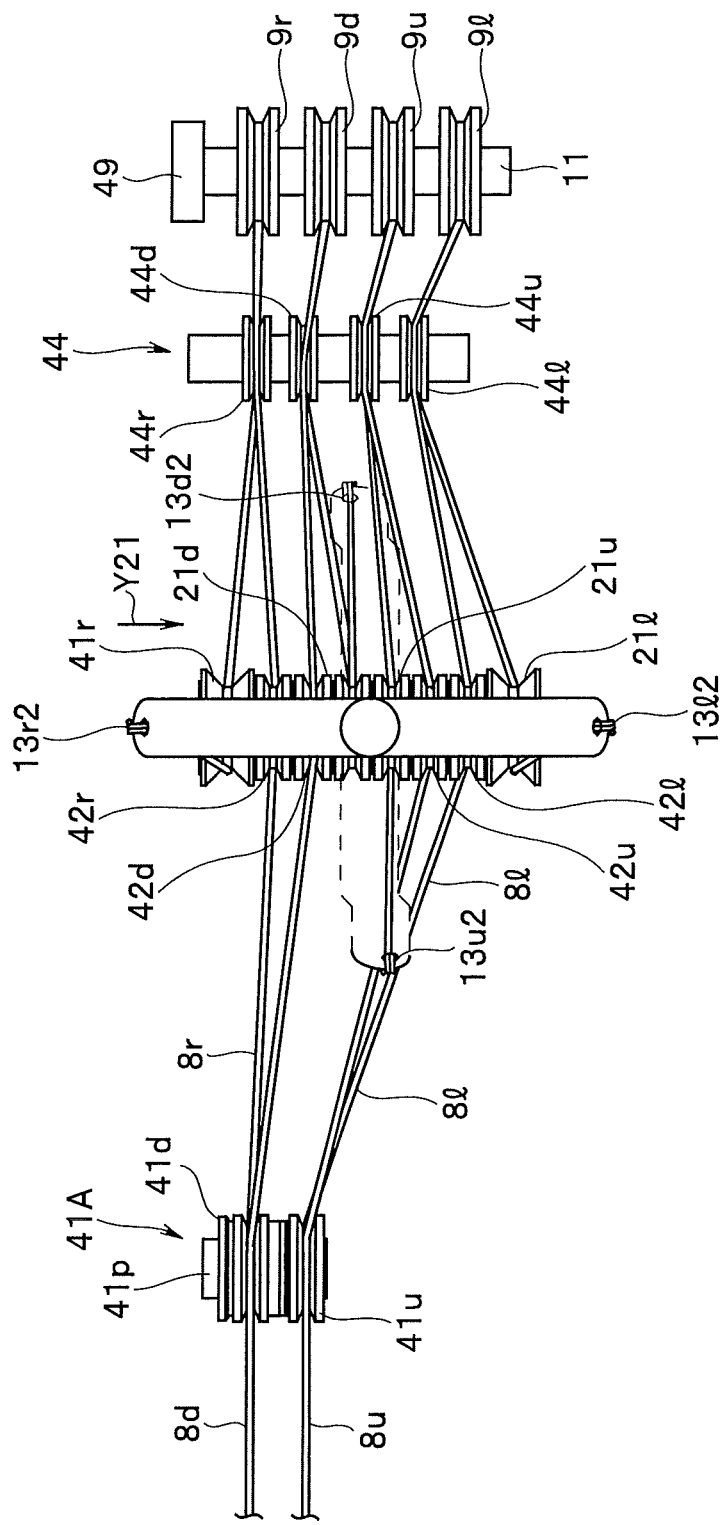
Figure 23:
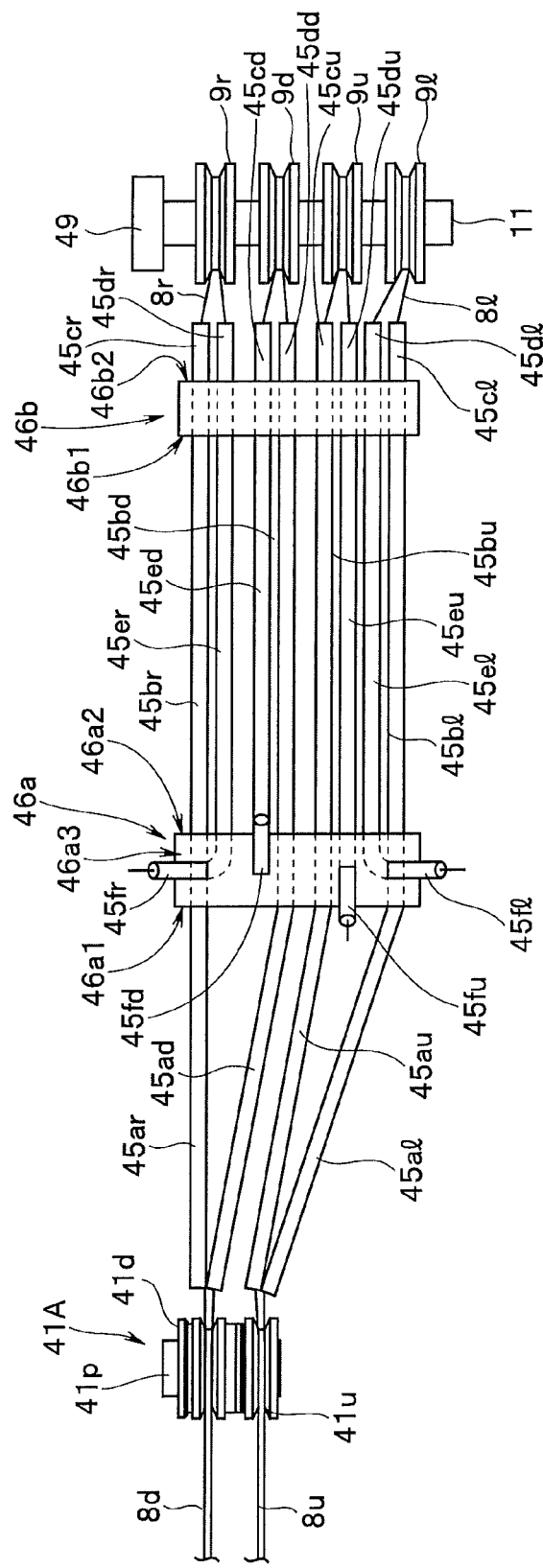
Figure 24:
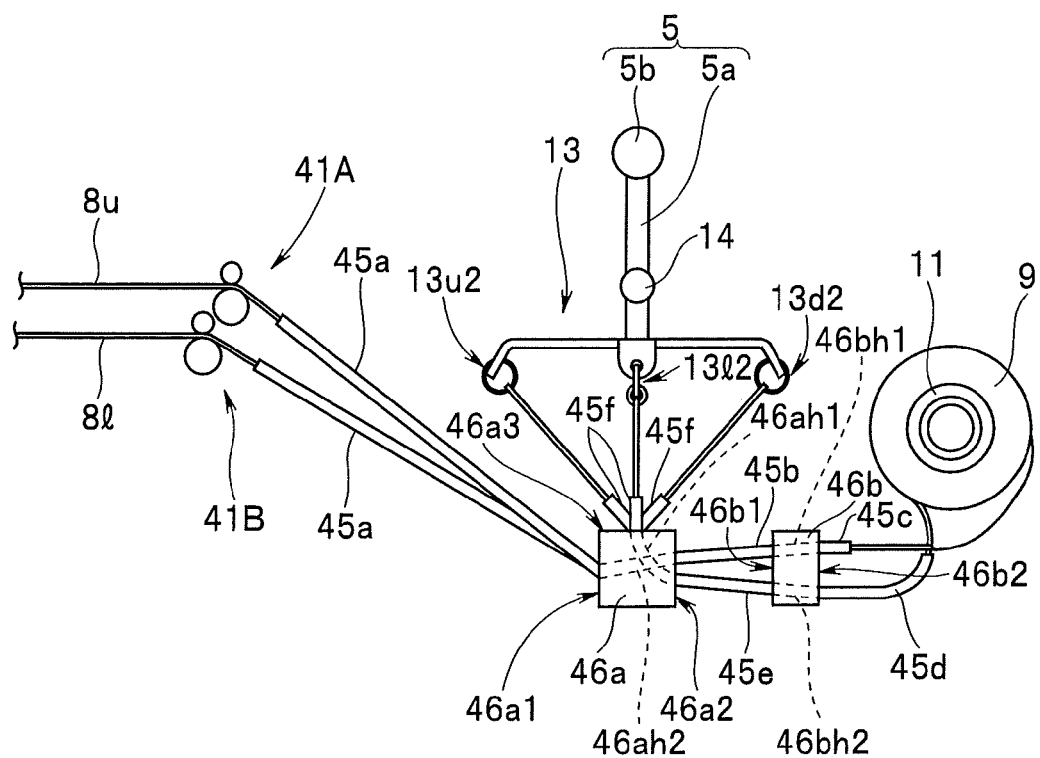

FIG. 16 to FIG. 24 relate to a third embodiment of the present invention. FIG. 16 is a view that illustrates an operation portion that includes a pulling member operation apparatus in which a motor having a motor shaft that is disposed so as to be orthogonal to a longitudinal axis of the operation portion, and a pulley having a pulley shaft that is disposed so as to be orthogonal to the longitudinal axis are contained in an operation portion body. FIG. 17 is a view that illustrates the pulling member operation apparatus that is provided inside the operation portion body. FIG. 18 is a perspective view that illustrates the configuration of the pulling member operation apparatus. FIG. 19 is a top view of the pulling member operation apparatus illustrated in FIG. 18. FIG. 20 is a side view of the pulling member operation apparatus illustrated in FIG. 18. FIG. 21 is a top view of a pulling member operation apparatus in which the arrangement positions of the guide rollers are different. FIG. 22 is a side view of the pulling member operation apparatus illustrated in FIG. 21. FIG. 23 is a top view of a pulling member operation apparatus in which coil pipes are used as travel path changing members. FIG. 24 is a side view of the pulling member operation apparatus shown in FIG. 23.

As shown in FIG. 16 and FIG. 17, an endoscope 1A of the present embodiment includes an insertion portion 2, an operation portion 3A, and a universal cord 4. An operation element 5 that is included in a pulling member operation apparatus 10C is erected vertically on the operation portion 3A. The insertion portion 2 includes a distal end portion 2a, a bending portion 2b, and a flexible tube portion 2c that are connected in series in that order from the distal end side. The operation portion 3A includes a grasping portion 3a that is connected in series to the insertion portion 2, and an operation portion body 3b1 that is connected in series to the grasping portion 3a. The operation element 5 that is used to perform an operation to cause the bending portion 2b to carry out a bending operation is provided inside the operation portion body 3b1.

In the endoscope 1A of the present embodiment also, the longitudinal axis of the insertion portion 2 and the longitudinal axis of the grasping portion 3a included in the operation portion 3A are set so as to be in a parallel positional relationship with each other. For example, as shown in FIG. 17, the longitudinal axis of the insertion portion 2 and the longitudinal axis of the grasping portion 3a are coaxial. Further, in the present embodiment, an axial line of the shaft portion 5a included in the operation element 5 and the longitudinal axis of the operation portion 3 are set in a mutually intersecting positional relationship.

In this connection, in addition to the operation element 5, for example, a switch (unshown) that is operated to input an instruction to perform various kinds of image pickup operations of an image pickup apparatus (unshown) that is provided inside the distal end portion 2a, an air/water supply button 6b1 and a suction button 6c1 are provided at predetermined positions on the exterior of the operation portion body 3b1. Further, a channel insertion port 6d is provided on the exterior of the grasping portion 3a.

The operation element 5 is provided at a position at which the operation element 5 is operated by a thumb of the hand of the operator which grasps the grasping portion 3a of the operation portion 3A in a case where the operator grasps the grasping portion 3a with the left hand in the same manner as for a conventional endoscope, and the air/water supply button 6b1 and the suction button 6c1 are provided at positions at which the air/water supply button 6b1 and the suction button 6c1 are operated by fingers other than the thumb of the hand with which the operator grasps the grasping portion 3a. Reference symbol 3b2 in FIG. 16 denotes an operation portion body casing that can be detached from a body portion 3b3 that is shown in FIG. 16 and FIG. 17.

The remaining configuration is the same as in the endoscope 1 of the above described embodiment, and in the following description the same members are denoted by the same reference symbols, and a description of such members is omitted.

The configuration and action of the pulling member operation apparatus 10C will now be described referring to FIG. 17 to FIG. 20.

The pulling member operation apparatus 10C is mainly constituted by the above described four bending wires 8u, 8d, 8l and 8r, four rotary bodies 9u, 9d, 9l and 9r, pulley 11, motor 12, hanging frame 13, and operation element 5, as well as a plurality of guide roller sets 41, 42, 43, and 44 that change the travel paths of the four wires 8u, 8d, 8l and 8r inside the operation portion 3.

In the present embodiment, the pulley 11 and the motor 12 are disposed at predetermined positions inside the operation portion body 3b1 so that the longitudinal axis of the pulley 11 and the drive shaft of the motor 12 are in a perpendicular positional relationship with respect to the longitudinal axis of the operation portion 3 (grasping portion 3a), respectively. Further, the pulley 11 and the motor 12 are separate elements, and as shown in FIG. 17, for example, the pulley 11 and the motor 12 are arranged side-by-side in the axis direction of the operation element 5.

A motor-side gear (unshown) is provided on a shaft (unshown) of the motor 12, and a pulley-side gear (see reference numeral 49 in FIG. 19) is provided at a predetermined position on the pulley 11. The pulley-side gear 49 is arranged so as to intermesh with the motor-side gear. The pulley 11 configured in this manner rotates around its axis when rotation of the motor 12 is transmitted to the pulley 11 through the motor-side gear and the pulley-side gear 49. That is, the motor-side gear and the pulley-side gear are driving force transmitting means.

In this connection, the motor 12 is not shown in FIG. 18 to FIG. 20, the pulley 11 is not shown in FIG. 18, and the upward frame 13u and the downward frame 13d of the hanging frame 13 are represented by a dashed line in FIG. 19. Further, the pulley 11 on which the four rotary bodies 9u, 9d, 9l and 9r are disposed is displaced further to the right direction in the drawings relative to the fourth guide roller set 44 to show the travel paths of the bending wires 8u, 8d, 8l and 8r.

The guide roller sets 41, 42, 43 and 44 that are wire travel path changing members of the present embodiment will now be described.

Reference symbols 41A and 41B shown in FIG. 18 and FIG. 19 denote the first guide roller set 41. Reference symbol 41A denotes a first guide roller set for the upward/downward directions (hereunder, abbreviated to "upward/downward guide roller set") 41A. The upward/downward guide roller set 41A includes a first roller shaft for the upward/downward directions 41p as a first support body, and two first guide rollers 41u and 41d. The two first guide rollers 41u and 41d are wire travel path changing members, and are pivotably disposed on the first roller shaft for the upward/downward directions 41p.

Reference symbol 41B denotes a first guide roller set for the left/right directions (hereunder, abbreviated to "left/right guide roller set") 41B. The left/right guide roller set 41B includes a first roller shaft for the left/right directions 41p as a first support body, and two first guide rollers 41l and 41r. The two first guide rollers 41l and 41r are wire travel path changing members, and are pivotably disposed on the first roller shaft for the left/right directions 41p.

The second guide roller set 42 includes a second roller shaft 42p, and second guide rollers 42u, 42d, 42l and 42r and guide rollers 21u, 21d, 21l and 21r. In the present embodiment, the two kinds of guide rollers, namely the second guide rollers 42u, 42d, 42l and 42r and the guide rollers 21u, 21d, 21l and 21r are pivotably disposed in a collective manner on the second roller shaft 42p. The second guide rollers 42u, 42d, 42l and 42r are wire travel path changing members, and are wire delivery members. The guide rollers 21u, 21d, 21l and 21r are attachment path setting member that are described above.

The third guide roller set 43 includes a third roller shaft 43p and third guide rollers 43u, 43d, 43l and 43r. The third guide rollers 43u, 43d, 43l and 43r are pivotably disposed on the third roller shaft 43p and change the wire travel paths. In the present embodiment, the third guide rollers 43u, 43d, 43l and 43r are pulley lead-in members.

The fourth guide roller set 44 includes a fourth roller shaft 44p and fourth guide rollers 44u, 44d, 44l and 44r. The fourth guide rollers 44u, 44d, 44l and 44r are pivotably disposed on the fourth roller shaft 43p and change the wire travel paths. In the present embodiment, the fourth guide rollers 44u, 44d, 44l and 44r are pulley lead-out members.

In the present embodiment, all of the roller shafts 41p, 42p, 43p and 44p are disposed at predetermined positions in an intersecting positional relationship with respect to the longitudinal axis of the operation portion 3. The second roller shaft 42p is disposed directly below the shaft portion 5a, and the center of the second roller shaft 42p is positioned on the central axis of the shaft portion 5a in an upright state.

The upward/downward guide roller set 41A and the left/right guide roller set 41B are disposed, for example, in a stacked arrangement in the axis direction of the operation element 5 inside the grasping portion 3a. Further, the upward/downward guide roller set 41A and the left/right guide roller set 41B are disposed at positions that are further to the distal end side than the operation element 5, in other words, at positions that are further to the distal end side than the second guide roller set 42.

The third guide roller set 43 and the fourth guide roller set 44 are disposed at positions that are further to the proximal end side than the operation element 5, in other words, at positions that are further to the proximal end side than the second guide roller set 42. The pulley 11 is disposed at a position that is furthest on the proximal end side. Specifically, the third guide roller set 43, the fourth guide roller set 44 and the pulley 11 are disposed in that order on the proximal end side from the operation element 5 side.

First guide rollers 41d and 41u are disposed in that order in the arrow Y19 direction on the first roller shaft for the upward/downward directions 41p of the upward/downward guide roller set 41A. Further, first guide rollers 41r and 41l are disposed in that order in the arrow Y19 direction on the first roller shaft for the left/right directions 41p of the left/right guide roller set 41B.

The third guide rollers 43r, 43d, 43u and 43l are disposed in that order in the arrow Y19 direction on the third roller shaft 43p. The fourth guide rollers 44r, 44d, 44u and 44l are disposed in that order in the arrow Y19 direction on the fourth roller shaft 44p. The rotary bodies 9r, 9d, 9u and 9l are disposed in that order in the arrow Y19 direction on the pulley 11.

The second guide rollers 42u, 42d, 42l and 42r and the guide rollers 21u, 21d, 21l and 21r are disposed in the following order in the arrow Y19 direction on the second roller shaft 42p of the second guide roller set 42.

Specifically, the order is guide roller for right 21r, second guide roller for right 42r, second guide roller for downward 42d, guide roller for downward 21d, guide roller for upward 21u, second guide roller for upward 42u, second guide roller for left 42l, and guide roller for left 21l.

In the present embodiment, the respective width dimensions and diameters of the guide roller for right 21r and the guide roller for left 21l that are disposed at the two ends are set to predetermined width dimensions and predetermined diameters that are wider than and larger than, respectively, the respective width dimensions and diameters of the other guide rollers 42u, 42d, 42l, 42r, 21u, and 21d that are disposed between the guide roller for right 21r and the guide roller for left 21l.

When the maximum external diameter of the guide roller for right 21r and the guide roller for left 21l is taken as w8, a relation between the maximum external diameter w8 and an interval w10 between the guide roller for right 21r and the guide roller for left 21l is set so that w10>w8.

Further, an interval between the guide roller for upward 21u and the guide roller for downward 21d is set to the interval w1 between the upward wire attachment portion 13u2 and the downward wire attachment portion 13d2 that is described above.

In addition, a relation between the interval w4 between the left wire attachment portion 13l2 and the right wire attachment portion 13r2 and the interval w10 between the outer end of the guide roller for right 21r and the outer end of the guide roller for left 21l that are disposed on the second roller shaft 42p is set so that w4>w10.

The wire travel paths within the operation portion 3 of the bending wires 8u, 8d, 8l and 8r will now be described referring to FIG. 18 to FIG. 20.

The respective bending wires 8u, 8d, 8l and 8r that are fixed to distal end bending pieces are extended inside the grasping portion 3a through guides (unshown). The bending wires 8u, 8d, 8l and 8r are guided to the first guide rollers 41u and 41d, of the upward/downward guide roller set 41A and the first guide rollers 41l and 41r of the left/right guide roller set 41B that are disposed in the grasping portion 3a, and the wire travel paths thereof are changed.

The respective bending wires 8u, 8d, 8l and 8r whose travel paths have been changed at the first guide rollers 41u, 41d, 41l and 41r are guided to the second guide rollers 42u, 42d, 42l and 42r of the second guide roller set 42, and the wire travel paths thereof are changed.

The respective bending wires 8u, 8d, 8l and 8r whose travel paths have been changed at the second guide rollers 42u, 42d, 42l and 42r are guided to the third guide rollers 43u, 43d, 43l and 43r of the third guide roller set 43, and the wire travel paths thereof are changed.

The respective bending wires 8u, 8d, 8l and 8r whose travel paths have been changed at the third guide rollers 43u, 43d, 43l and 43r are guided to the winding start positions 9s of the respective rotary bodies 9u, 9d, 9l and 9r that are disposed in a slackened state on the pulley 11.

The bending wires 8u, 8d, 8l, and 8r that have been guided to the winding start positions 9s of the respective rotary bodies 9u, 9d, 9l and 9r are wound around the respective rotary bodies 9u, 9d, 9l and 9r in a predetermined slackened state, and are extended from the respective winding end positions 9e.

The respective bending wires 8u, 8d, 8l and 8r that have been extended from the winding end positions 9e of the respective rotary bodies 9u, 9d, 9l and 9r are guided to the fourth guide rollers 44u, 44d, 44l and 44r of the fourth guide roller set 44, and the wire travel paths thereof are changed.

The respective bending wires 8u, 8d, 8l and 8r whose travel paths have been changed at the fourth guide rollers 44u, 44d, 44l and 44r are guided to the guide rollers 21u, 21d, 21l and 21r of the second guide roller set 42, and the wire travel paths are changed to guide the respective bending wires 8u, 8d, 8l and 8r to the wire attachment portions 13u2, 13d2, 13l2 and 13r2, and the respective bending wires 8u, 8d, 8l and 8r are fixed thereto.

In this connection, according to the present embodiment, the third guide rollers 43u, 43d, 43l and 43r are disposed facing the rotary bodies 9u, 9d, 9l and 9r in a manner that takes into consideration the winding start positions 9s of the rotary bodies 9u, 9d, 9l and 9r. As a result, the respective bending wires 8u, 8d, 8l and 8r are smoothly wound around the respective rotary bodies 9u, 9d, 9l and 9r.

In contrast, the fourth guide rollers 44u, 44d, 44l and 44r are disposed in a manner that takes into consideration the winding end positions 9e of the rotary bodies 9u, 9d, 9l and 9r and the positions of the guide rollers 21u, 21d, 21l and 21r. As a result, the travel paths of the bending wires 8u, 8d, 8l and 8r that are extended from the winding end positions 9e can be smoothly changed at the third guide rollers 43u, 43d, 43l and 43r towards the guide rollers 21u, 21d, 21l and 21r of the second guide roller set 42.

Further, when the shaft portion 5a of the operation element 5 is in an upright state, the bending wires 8u, 8d, 8l and 8r that extend from the guide rollers 21u, 21d, 21l and 21r towards the hanging frame 13 are all in a predetermined slackened state. In this connection, a configuration may also be adopted in which partition members 48 that are shown in FIG. 20 are provided between adjacent bending wires 8 to prevent the bending wires 8 from tangling together.

Thus, in the configuration in which the pulley 11 and the motor 12 are disposed at positions that are furthest on the proximal end side of the operation portion 3 that includes the grasping portion 3a that has a longitudinal axis that is parallel to the longitudinal axis of the insertion portion 2 included in the endoscope 1A, the longitudinal axis of the pulley 11 and the drive shaft of the motor 12 are disposed in a perpendicular positional relationship with respect to the longitudinal axis of the operation portion 3. In addition, the guide roller sets 41, 42, 43 and 44 are disposed at predetermined positions as wire travel path changing members.

Further, the travel paths of the respective bending wires 8u, 8d, 8l and 8r that are led into the operation portion 3 and travel towards the proximal end side of the operation portion 3 are changed by the first guide rollers 41u, 41d, 41l and 41r, the second guide rollers 42u2, 42d2, 42l2 and 42r2, and the third guide rollers 43u, 43d, 43l and 43r so that the travel paths change in the direction of the winding start positions 9s of the rotary bodies 9u, 9d, 9l and 9r that are disposed on the pulley 11.

Next, the travel paths of the respective bending wires 8u, 8d, 8l and 8r that are led out from the respective winding end positions after being wound around the rotary bodies 9u, 9d, 9l and 9r are changed by the fourth guide rollers 44u, 44d, 44l and 44r and the guide rollers 21u, 21d, 21l and 21r and led and fixed to the wire attachment portions 13u2, 13d2, 13l2 and 13r2 of the hanging frame 13 that is fixed to the shaft portion 5a of the operation element 5.

According to the endoscope 1A configured in the above manner, in a state in which the motor 12 is driven and the pulley 11 is rotated, when the shaft portion 5a of the operation element 5 is in an upright state each of the bending wires 8u, 8d, 8l and 8r that are wound around the rotary bodies 9u, 9d, 9l and 9r disposed on the pulley 11, respectively, enters a predetermined slackened state. As a result, similarly to the case described above, the bending portion 2b is maintained in a straight state.

On the other hand, in a state in which the operator has grasped the grasping portion 3a, to cause the bending portion 2b to perform a bending operation in, for example, the upward direction, the operator tilts the operation element 5 in the direction of the arrow Yu in FIG. 16. Thereupon, accompanying the operation to tilt the operation element 5, the hanging frame 13 inclines, and the upward bending wire 8u that is fixed to the upward wire attachment portion 13u2 as described above gradually changes from a slackened state to a tensed state and the bending portion 2b bends in the upward direction.

In contrast, if the operator continues to maintain the tilt position of the operation element 5, as described above, the tensed state of the upward bending wire 8u and the slackened state of the bending wires 8d, 8l and 8r are maintained and thus the bent state of the bending portion 2b is maintained. Subsequently, if the operator performs a tilt operation with respect to the operation element 5 to bend the bending portion 2b further in the same direction, to bend the bending portion 2b in another direction, or to return the bending portion 2b to the original state thereof, the bending wires 8u, 8d, 8l and 8r are pulled or slackened in accordance with the tilt operation, and the bending portion 2b changes to a state that corresponds to the tilt operation of the operation element 5.

According to this configuration, by using the first guide rollers 41u, 41d, 41l and 41r, the second guide rollers 42u, 42d, 42l and 42r, the third guide rollers 43u, 43d, 43l and 43r, the fourth guide rollers 44u, 44d, 44l and 44r, and the guide rollers 21u, 21d, 21l and 21r to change the wire travel paths of the bending wires 8u, 8d, 8l and 8r that are led into the operation portion 3, the end portions of the bending wires 8u, 8d, 8l and 8r can be fixed to the wire attachment portions 13u2, 13d2, 13l2 and 13r2 of the hanging frame 13 that is fixed to the shaft portion 5a of the operation element 5 having an axis line that intersects with the longitudinal axis of the operation portion 3, and the bending wires 8u, 8d, 8l and 8r can be smoothly pulled/slackened by a tilt operation of the operation element 5.

Further, according to the endoscope 1A, in a state in which the operator has grasped the operation portion 3A, that is, during endoscopy, the operator can easily operate not just the operation element 5, but also the air/water supply button 6b, the suction button 6c and the switch 6a.

In this connection, in the above described embodiment, the second guide rollers 42u, 42d, 42l and 42r and the guide rollers 21u, 21d, 21l and 21r are disposed on the second roller shaft 42p of the second guide roller set 42.

However, as shown in FIG. 21 and FIG. 22, a configuration may also be adopted in which, instead of the second guide roller set 42 on which two kinds of guide rollers are disposed, a second guide roller set 42A on which only the second guide rollers 42u, 42d, 42l and 42r are disposed and a guide roller set 21 on which only the guide rollers 21u, 21d, 21l and 21r are disposed are arranged as separate elements at predetermined positions.

Further, instead of adopting a configuration that changes the wire travel paths by providing a plurality of guide rollers, a configuration may be adopted that changes the wire travel paths by disposing a plurality of coils pipes in the manner shown in FIG. 23 and FIG. 24.

In the embodiment shown in FIG. 21 and FIG. 22, the second guide roller set 42 is divided into the second guide roller set 42A in which the second guide rollers 42u, 42d, 42l and 42r are disposed at predetermined positions on the second roller shaft 42p1, and the guide roller set 21 in which the guide rollers 21u, 21d, 21l and 21r are disposed at predetermined position on the roller shaft 21p.

Further, as shown in FIG. 22, the second guide roller set 42A is disposed directly below the guide roller set 21. In this arrangement state, as shown by the arrow Y21 in FIG. 21, the guide rollers 21u, 21d, 21l and 21r and the second guide rollers 42u, 42d, 42l and 42r are disposed in the order of guide roller for right 21*r*, second guide roller for right 42*r*, second guide roller for downward 42*d*, guide roller for downward 21*d*, guide roller for upward 21*u*, second guide roller for upward 42*u*, second guide roller for left 42*l*, and guide roller for left 21*l*.

According to this configuration, instead of providing the third guide roller set 43 and the fourth guide roller set 44, the fourth guide roller set 44 is disposed at a predetermined position with respect to the rotary bodies 9*u*, 9*d*, 9*l* and 9*r* of the pulley 11 as a single dual-purpose guide roller set that is used as both the third guide roller set 43 and the fourth guide roller set 44. That is, the third guide rollers 43*u*, 43*d*, 43*l* and 43*r* of the third guide roller set 43 are removed, and the fourth guide rollers 44*u*, 44*d*, 44*l* and 44*r* are used both as pulley lead-in members and pulley lead-out members.

Therefore, the fourth guide rollers 44 of the fourth guide roller set 44 are disposed in a manner that takes into consideration the winding start positions 9*s* of the rotary bodies 9*u*, 9*d*, 9*l* and 9*r*, and are also disposed in a manner that takes into consideration the winding end positions 9*e* of the rotary bodies 9*u*, 9*d*, 9*l* and 9*r*, the first shaft body 112, and the position of the guide roller set 21. As a result, the respective bending wires 8*u*, 8*d*, 8*l* and 8*r* are smoothly wound around the rotary bodies 9*u*, 9*d*, 9*l* and 9*r*, and the travel paths of the respective bending wires 8*u*, 8*d*, 8*l* and 8*r* that are extended from the winding end positions 9*e* of the respective rotary bodies 9*u*, 9*d*, 9*l* and 9*r* can be smoothly changed in the direction of the guide rollers 21*u*, 21*d*, 21*l* and 21*r* of the guide roller set 21.

The wire travel paths inside the operation portion 3 of the bending wires 8*u*, 8*d*, 8*l* and 8*r* will now be described referring to FIG. 21 and FIG. 22.

In the present embodiment also, the bending wires 8*u*, 8*d*, 8*l* and 8*r* are extended within the grasping portion 3*a* through guides (unshown). Further, the bending wires 8*u*, 8*d*, 8*l* and 8*r* are guided to the first guide rollers 41*u* and 41*d* of the upward/downward guide roller set 41A and the first guide rollers 41*l* and 41*r* of the left/right guide roller set 41B that are disposed in the grasping portion 3*a*, and the wire travel paths are changed.

The respective bending wires 8*u*, 8*d*, 8*l* and 8*r* whose travel paths have been changed at the first guide rollers 41*u*, 41*d*, 41*l* and 41*r* are guided to the second guide rollers 42*u*, 42*d*, 42*l* and 42*r* of the second guide roller set 42A, and the wire travel paths are changed.

The respective bending wires 8*u*, 8*d*, 8*l* and 8*r* whose travel paths have been changed at the second guide rollers 42*u*, 42*d*, 42*l* and 42*r* are guided to the fourth guide rollers 44*u*, 44*d*, 44*l* and 44*r* of the fourth guide roller set 44, and the wire travel paths are changed.

The respective bending wires 8*u*, 8*d*, 8*l* and 8*r* whose travel paths have been changed at the fourth guide rollers 44*u*, 44*d*, 44*l* and 44*r* are guided to the winding start positions 9*s* of the rotary bodies 9*u*, 9*d*, 9*l* and 9*r* that are disposed in a slackened state on the pulley 11.

The respective bending wires 8*u*, 8*d*, 8*l* and 8*r* that have been guided to the winding start positions 9*s* of the rotary bodies 9*u*, 9*d*, 9*l* and 9*r* are wound around the respective rotary bodies 9*u*, 9*d*, 9*l* and 9*r* so as to enter a predetermined slackened state, and are extended from the respective winding end positions 9*e*.

The respective bending wires 8*u*, 8*d*, 8*l* and 8*r* that have been extended from the winding end positions 9*e* of the respective rotary bodies 9*u*, 9*d*, 9*l* and 9*r* are again guided to the fourth guide rollers 44*u*, 44*d*, 44*l* and 44*r* of the fourth guide roller set 44, and the wire travel paths are changed.

The respective bending wires 8*u*, 8*d*, 8*l* and 8*r* whose travel paths have been changed at the fourth guide rollers 44*u*, 44*d*, 44*l* and 44*r* are guided to the guide rollers 21*u*, 21*d*, 21*l* and 21*r* of the guide roller set 21, at which the wire travel paths are changed, and are then guided and fixed to the wire attachment portions 13*u*2, 13*d*2, 13*l*2 and 13*r*2.

In the present embodiment, by eliminating the third guide roller set 43 and causing the fourth guide roller set 44 to have the above described travel path changing function of the third guide roller set 43 in addition to the travel path changing function of the fourth guide roller set 44, the number of components can be decreased and the size of the operation portion body can be reduced. The other actions and effects are the same as in the above described third embodiment.

In the embodiment shown in FIG. 23 and FIG. 24, instead of providing a plurality of guide roller sets to change the travel paths of the bending wires 8, the travel paths of the bending wires 8 are changed by providing the first guide roller set 41, a plurality of coil pipes 45*a*, 45*b*, 45*c*, 45*d*, and 45*e*, and a plurality of coil pipe brackets 46*a* and 46*b*.

In this case, the coil pipes 45*a*, 45*b*, 45*c*, 45*d* and 45*e* are travel path changing members and, for example, are made of metal. Each of the coil pipes 45*a*, 45*b*, 45*c*, 45*d* and 45*e* has a through-hole through which the bending wire 8 can be inserted so as to freely advance and retract.

The first coil pipe bracket 46*a* is a rectangular parallelepiped shape, and is disposed directly below the operation element 5. A plurality of pipe connection ports (unshown) are provided in a first face 46*a*1, a second face 46*a*2, and a third face 46*a*3 of the first coil pipe bracket 46*a*. Predetermined pipe connection ports communicate with each other through communicating holes 45*ah*1 and 45*ah*2.

The second coil pipe bracket 46*b* is a rectangular parallelepiped shape, and is disposed in the vicinity of the pulley 11. Eight pipe connection ports (unshown) are provided on a first face 46*b*1 and a second face 46*b*2 of the second coil pipe bracket 46*b*, respectively. Predetermined pipe connection ports communicate with each other through communicating holes 46*bh*1 and 46*bh*2.

The first coil pipes 45*a* guide the bending wires 8 to a first communicating hole 46*ah*1 of the first coil pipe bracket 46*a*. The first coil pipes 45*a* are disposed between the first guide roller set 41 and the first coil pipe bracket 46*a*. The distal end portions of the first coil pipes 45*a* are provided in the vicinity of the first guide rollers 41*u* and 41*d* of the upward/downward guide roller set 41A and the vicinity of the first guide rollers 41*l* and 41*r* of the left/right guide roller set 41B. The proximal end portions of the first coil pipes 45*a* are fixed to pipe connection ports provided in the first face 46*a*1 of the first coil pipe bracket 46*a*.

The second coil pipes 45*b* guide the bending wires 8 from the first communicating hole 46*ah*1 of the first coil pipe bracket 46*a* to a first communicating hole 46*bh*1 of the second coil pipe bracket 46*b*. The distal end portions of the second coil pipes 45*b* are fixed to pipe connection ports provided in the second face 46*a*2 of the first coil pipe bracket 46*a*. The proximal end portions of the second coil pipes 45*b* are fixed to pipe connection ports provided in the first face 46*b*1 of the second coil pipe brackets 46*b*.

The third coil pipes 45*c* guide the bending wires 8 to winding start positions 9*s* of the rotary bodies 9 disposed on the pulley 11. The distal end portions of the third coil pipe 45*c* are fixed to pipe connection ports provided in the second face 46*b*2 of the second coil pipe bracket 46*b*. Openings of the proximal end portions of the third coil pipes 45*c* are disposed at predetermined positions facing the winding start positions 9s of the rotary bodies 9u, 9d, 9l and 9r. The third coil pipes 45c are pulley lead-in members.

The fourth coil pipes 45d guide the bending wires 8 that are extended from the winding end positions 9e of the rotary bodies 9 to a second communicating hole 46bh2 of the second coil pipe bracket 46b. The distal end portions of the fourth coil pipes 45d are fixed to pipe connection ports provided in the second face 46b2 of the second coil pipe bracket 46b. Openings of the proximal end portions of the fourth coil pipes 45d are disposed at predetermined positions facing the winding end positions 9e of the rotary bodies 9u, 9d, 9l and 9r. The fourth coil pipes 45d are pulley lead-out members.

The fifth coil pipes 45e guide the bending wires 8 from the second communicating hole 46bh2 of the second coil pipe bracket 46b to the second communicating hole 46ah2 of the first coil pipe bracket 46a. The distal end portions of the fifth coil pipes 45e are fixed to pipe connection ports provided in the second face 46a2 of the first coil pipe bracket 46a. The proximal end portions of the fifth coil pipes 45e are fixed to pipe connection ports provided in the first face 46b1 of the second coil pipe bracket 46b.

The sixth coil pipes 45f guide the bending wires 8 that are extended from the second communicating hole 46ah2 of the first coil pipe bracket 46a to the wire attachment portions 13u2, 13d2, 13l2 and 13r2 of the hanging frame 13. The proximal end portions of the sixth coil pipes 45f are fixed to pipe connection ports provided in the third face 46a3 of the first coil pipe bracket 46a. Openings of the distal end portions of the sixth coil pipes 45f are disposed at predetermined positions facing the wire attachment portions 13u2, 13d2, 13l2 and 13r2. The sixth coil pipes 45f are attachment path setting members.

The wire travel paths of the bending wires 8 inside the operation portion 3 will now be described referring to FIG. 23 and FIG. 24.

According to the present embodiment also, the respective bending wires 8u, 8d, 8l and 8r are extended inside the grasping portion 3a through guides (unshown). The bending wires 8u, 8d, 8l and 8r are guided to the first guide rollers 41u and 41d of the upward/downward guide roller set 41A and the first guide rollers 41l and 41r of the left/right guide roller set 41B that are disposed in the grasping portion 3a, at which the wire travel paths are changed.

For example, after the travel path of the upward bending wire 8u has been changed at the first guide roller 41u, the upward bending wire 8u is led into a through-hole of a first coil pipe for the upward direction 45au. Thereafter, the upward bending wire 8u passes through the first communicating hole 46ah1 of the first coil pipe bracket 46a, a through-hole of a second coil pipe for the upward direction 45bu, the first communicating hole 46bh1 of the second coil pipe bracket 46b, and a through-hole of a third coil pipe for the upward direction 45cu, and is guided to the winding start position 9s of the upward rotary body 9u that is disposed in a slackened state on the pulley 11.

Thereafter, the upward bending wire 8u that has been guided to the winding start position 9s of the upward rotary body 9u is wound around the upward rotary body 9u so as to be in a predetermined slackened state, and is extended from the winding end position 9e.

The upward bending wire 8u that is extended from the winding end position 9e of the upward rotary body 9u is led into a through-hole of a fourth coil pipe for the upward direction 45du. Thereafter, the upward bending wire 8u passes through the second communicating hole 46bh2 of the second coil pipe bracket 46b, a through-hole of a fifth coil pipe for the upward direction 45eu, the second communicating hole 46ah2 of the first coil pipe bracket 46a, and a through-hole of a sixth coil pipe for the upward direction 45fu, and arrives at the vicinity of the wire attachment portion 13u2 to be fixed thereto.

With respect to the other bending wires 8d, 8l and 8r also, similarly to the upward bending wire 8u, after the travel paths have been changed at the respective first guide rollers 41d, 41l and 41r, the bending wires 8d, 8l and 8r are led into through-holes of the respective first coil pipes 45a, and pass through through-holes of the third coil pipes 45c and are wound around the respective rotary bodies 9d, 9l and 9r. Thereafter, the bending wires 8d, 8l and 8r are led into through-holes of the respective fourth coil pipes 45d, and pass through through-holes of the sixth coil pipes 45f and arrive at the vicinity of the wire attachment portions 13d2, 13l2 and 13r2 and are fixed to the respective wire attachment portions 13d2, 13l2 and 13r2.

According to this configuration, after the travel paths of the bending wires 8u, 8d, 8l and 8r are changed at the first guide rollers 41u, 41d, 41l and 41r of the first guide roller set 41, the bending wires 8u, 8d, 8l and 8r are led into through-holes of the first coil pipes 45a that correspond to the respective bending wires 8, and are wound around the respective rotary bodies 9u, 9d, 9l and 9r. Next, the bending wires 8u, 8d, 8l and 8r are led into through-holes of the respective fourth coil pipes 45d, and thereafter fixed to the wire attachment portions 13u2, 13d2, 13l2 and 13r2, respectively.

As a result, entanglement between the bending wires 8 whose wire travel paths are changed inside the operation portion 3 can be reliably prevented.

In this connection, a configuration may also be adopted in which the first guide rollers 41u, 41d, 41l and 41r are not provided and the first coil pipes 45a are extended to the distal end side of the insertion portion 2. The other actions and effects are the same as the above described third embodiment.

Figure 25:
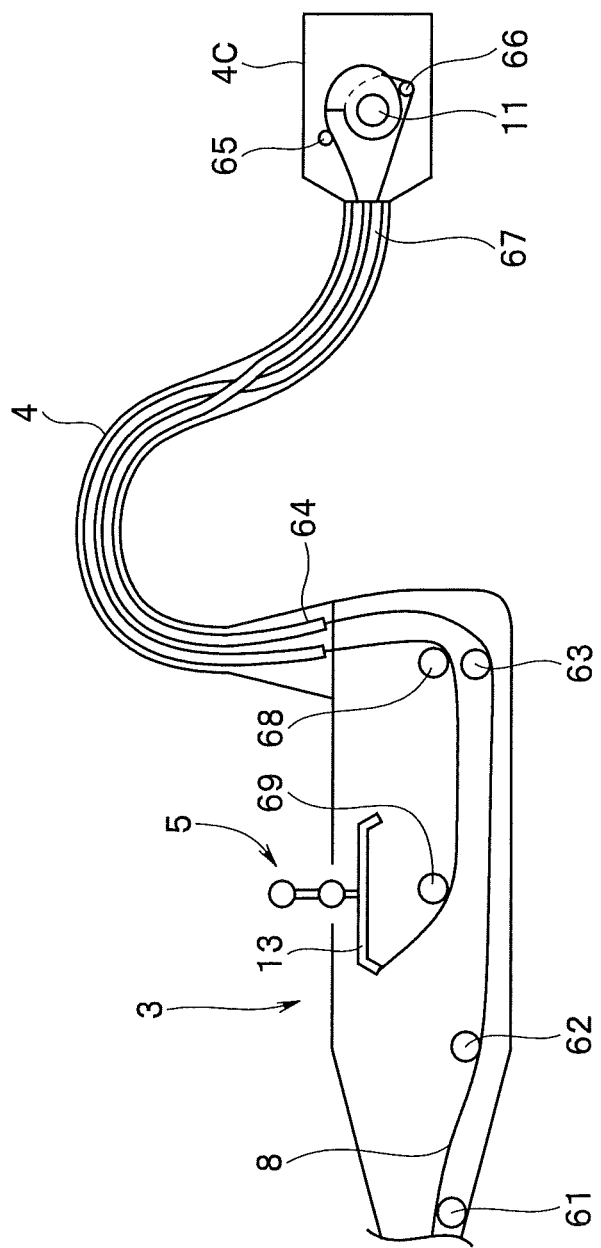
FIG. 25 is a view that illustrates a configuration example of a pulling member operation apparatus that is disposed inside a connector that is provided in a proximal end portion of a universal cord in which a pulley and a motor are outside an operation portion.

In the above described embodiment, the pulley 11 and the motor 12 are disposed inside the operation portion 3. However, the arrangement positions of the pulley 11 and the motor 12 are not limited to the inside of the operation portion 3, and as shown in FIG. 25, a configuration may also be adopted in which the pulley 11 and the motor (unshown) are arranged inside a connector 4c that is provided at a proximal end portion of the universal cord 4.

According to this configuration, the bending wire 8 is extended into the grasping portion 3a through a guide (unshown), the wire travel path thereof is changed by a plurality of guide roller sets 61, 62, 63 and the like that are disposed in the grasping portion 3a to thereby guide the bending wire 8 into the universal cord 4. Thereafter, the bending wire 8 passes through a first coil pipe 64 disposed inside the universal cord 4, and the travel path is then changed by a guide roller set 65 so that the bending wire 8 is guided to the winding start position 9s of the rotary body 9 disposed in a slackened state on the pulley 11.

Further, the bending wire 8 that has been guided to the winding start position 9s of the rotary body 9 is wound around the rotary body 9 so as to be in a predetermined slackened state, and is extended from the winding end position 9e.

The travel path of the bending wire 8 that has been extended from the winding end position 9e of the rotary body 9 is changed by the guide roller set 66 so that the bending wire 8 is guided into the operation portion 3 through a second coil pipe 67 disposed inside the universal cord 4.

Thereafter, the wire travel path of the bending wire 8 is changed by a plurality of guide roller sets 68, 69 and the like, and the bending wire 8 arrives at the vicinity of the wire attachment portion 13$u$2 and is fixed thereto.

According to this configuration, the weight of the operation portion 3 can be reduced by disposing the pulley 11 and the motor 12 that were disposed inside the operation portion 3 in the above configuration, inside the connector 4$c$. The other actions and effects are the same as in the above described third embodiment.

It should be understood that the present invention is not limited to only the above described embodiments, and various changes and modifications thereof can be made without departing from the spirit or scope of the invention.

What is claimed is:

1. A bending apparatus comprising:
   a bending portion provided to an insertion portion to be inserted in a subject, the bending portion being bendable in a plurality of bending directions;
   an operation portion including an operation portion body at which a bending operation of the bending portion is performed, and a grasping portion to be grasped by an operator, the grasping portion being connected to the operation portion body and having a longitudinal axis parallel to an insertion axis of the insertion portion;
   an operation element that is erected vertically from the operation portion body, the operation element having a shaft portion that allows tilting operation by the operator to input a bending operation;
   a hanging frame that extends in a diameter direction from the shaft portion of the operation element inside the operation portion;
   a plurality of pulling members each having one end and another end, the one end being connected to the bending portion, the other end being connected to the hanging frame, the plurality of pulling members being provided to respectively correspond to the plurality of bending directions;
   a pulley disposed inside the operation portion, wherein a plurality of rotary bodies, around which intermediate portions of the plurality of pulling members are wound, are disposed on the pulley;
   a motor disposed inside the operation portion, wherein the motor rotates the pulley to generate a driving force to rotate the plurality of rotary bodies in order to pull the plurality of pulling members would around the plurality of rotary bodies—in a winding direction;
   a first guide roller that changes a travel path of a first pulling member corresponding to a first bending direction of the plurality of bending directions, the first pulling member being included in the plurality of pulling members, the first guide roller being arranged rotatably on a support body, a center of the support body being positioned on a central axis of the shaft portion which is in an upright state; and
   a second guide roller that changes a travel path of a second pulling member corresponding to a second bending direction of the plurality of bending directions, the second pulling member being included in the plurality of pulling members, the second guide roller being arranged rotatably on the support body,
   wherein the first guide roller is configured to have a diameter larger than a diameter of the second guide roller, and
   the second guide roller is arranged at a position closer to the center of the support body than the first guide roller.

2. The bending apparatus according to claim 1, wherein the first guide roller and the second guide roller are arranged adjacent to the hanging frame in a direction perpendicular to the longitudinal axis of the grasping portion.

3. The bending apparatus according to claim 1, wherein;
   the motor is arranged parallel to the longitudinal axis of the grasping portion.

4. The bending apparatus according to claim 1, wherein;
   the pulley includes a first pulley and a second pulley that are disposed parallel to each other, and a rotary shaft of each of the pulleys is disposed inside the grasping portion in a perpendicular positional relationship with respect to the longitudinal axis of the grasping portion; and
   the motor is disposed inside the grasping portion such that a drive shaft of the motor is in a coaxial, parallel, or perpendicular positional relationship with respect to the longitudinal axis of the grasping portion;
   the bending apparatus further comprising:
   a driving force transmitting mechanism portion that has a gear train comprising a plurality of gears and that transmits the driving force of the motor to the pulleys; and
   pulley lead-in members that divide travel paths of the plurality of pulling members that are guided into the operation portion into two paths and guide the pulling members to the first pulley and the second pulley, or pulley lead-out members that guide a travel path of the first pulling member that is extended from the first pulley to the first guide roller and guide a travel path of the second pulling member that is extended from the second pulley to the second guide roller.

5. The bending apparatus according to claim 4, wherein the first pulley and the second pulley are rotated in opposite directions to each other by the driving force transmitting mechanism portion, and a winding direction of the first pulling member that is wound around the first pulley and a winding direction of the second pulling member that is wound around the second pulley are different to each other.

6. The bending apparatus according to claim 4, wherein the first pulley and the second pulley are rotated in identical directions by the driving force transmitting mechanism portion, and a winding direction of the first pulling member that is wound around the first pulley and a winding direction of the second pulling member that is wound around the second pulley are identical directions.

7. The bending apparatus according to claim 5, wherein;
   the pulley lead-in member, the pulley lead-out member, the first guide roller, and the second guide roller are each provided in plurality in correspondence with the plurality of pulling members; and
   the plurality of pulley lead-in members and the plurality of pulley lead-out members are assembled such that the plurality of pulley lead-in members and the plurality of pulley lead-out members are divided into two first support bodies and two second support bodies, respectively, in correspondence with the first pulling member that is wound around the first pulley and the second pulling member that is wound around the second pulley, and the plurality of first guide rollers and the plurality of second guide rollers are disposed at predetermined positions inside the operation portion in a state of being pivotably assembled on the support bodies.

8. The bending apparatus according to claim 7, wherein the plurality of pulley lead-in members disposed on one of the first support bodies and the plurality of pulley lead-out members disposed on one of the second support bodies, and the plurality of pulley lead-in members disposed on the other of the first support bodies and the plurality of pulley lead-out members disposed on the other of the second support bodies are disposed at facing positions such that a hypothetical line that joins a center of the first pulley and a center of the second pulley is interposed therebetween, and the support bodies on which the plurality of first guide rollers and the plurality of second guide rollers are disposed are disposed in an intersecting positional relationship with respect to a longitudinal axis of the operation portion.

* * * * *